US012653859B2

(12) United States Patent
Ruvo et al.

(10) Patent No.: US 12,653,859 B2
(45) Date of Patent: Jun. 16, 2026

(54) PEPTIDES AND MEDICAL USES THEREOF

(71) Applicant: Anbition S.R.L., Naples (IT)

(72) Inventors: Menotti Ruvo, San Nicola alla Strada (IT); Davide Rosiello, Naples (IT); Sandro De Falco, Naples (IT)

(73) Assignee: ANBITION S.R.L., Naples (IT)

( * ) Notice: Subject to any disclaimer, the term of this patent is extended or adjusted under 35 U.S.C. 154(b) by 1259 days.

(21) Appl. No.: 17/275,029

(22) PCT Filed: Sep. 11, 2019

(86) PCT No.: PCT/IB2019/057637
§ 371 (c)(1),
(2) Date: Mar. 10, 2021

(87) PCT Pub. No.: WO2020/053773
PCT Pub. Date: Mar. 19, 2020

(65) Prior Publication Data

US 2022/0054583 A1 Feb. 24, 2022

(30) Foreign Application Priority Data

Sep. 11, 2018 (IT) ........................ 102018000008507

(51) Int. Cl.

| | |
|---|---|
| ***A61K 38/10*** | (2006.01) |
| ***A61K 9/00*** | (2006.01) |
| ***A61K 38/00*** | (2006.01) |
| ***A61P 19/00*** | (2006.01) |
| ***A61P 27/02*** | (2006.01) |
| ***C07K 7/06*** | (2006.01) |
| ***C07K 14/00*** | (2006.01) |

(52) U.S. Cl.
CPC ............ *A61K 38/10* (2013.01); *A61K 9/0053* (2013.01); *A61P 27/02* (2018.01)

(58) Field of Classification Search
CPC ........ A61K 38/10; A61K 9/0053; A61P 27/02
See application file for complete search history.

(56) References Cited

U.S. PATENT DOCUMENTS

2012/0329707 A1 12/2012 DiMarchi et al.

FOREIGN PATENT DOCUMENTS

| | | | |
|---|---|---|---|
| EP | 0987274 | A1 | 3/2000 |
| WO | 2001085796 | A2 | 11/2001 |

OTHER PUBLICATIONS

Bhattacharya et al., PLoS ONE 12(3): e0171355. https://doi.org/10.1371/journal.pone.0171355; 22 pages total (Year: 2017).*

Fenton et al., Medicinal Chemistry Research (2020) 29:1133-1146 (Year: 2020).*

Hereditary Optic Neuropathies, Merck Manuals, accessed Mar. 27, 2017 at URL merckmanuals.com/professional/eye-disorders/optic-nerve-disorders/hereditary-optic-neuropathies, pp. 1-2 (2017) (Year: 2017).*

Diabetic retinopathy, Merck—accessed Jul. 3, 2021 at URL: merckmanuals.com/professional/eye-disorders/retinal-disorders/diabetic-retinopathy?query=ocular neovascular, 5 pages (Year: 2021).*

Emerson et al., "Emerging therapies for the treatment of neovascular age-related macular degeneration and diabetic macular edema," Biodrugs 21:245-257 (2007) (Year: 2007).*

Hartong et al., "Retinitis pigmentosa," Lancet 368:1795-1809 (2006) (Year: 2006).*

Nita et al, "Age-related macular degeneration and changes in the extracellular matrix," Med Sci Monit 20: 1003-1016 (2014) (Year: 2014).*

Auerbach et al., "Angiogenesis assays: Problems and pitfalls," Cancer and Metastasis Reviews, 2000, 19: 167-172. (Year: 2000).*

Jain RK, "Barriers to Drug Delivery in Solid Tumors," Scientific American, 1994, 58-65. (Year: 1994).*

Patel et al, "A Review: Formulation of Fast Dissolving Tablet," PharmaTutor 2(3):30-46 (2014) (Year: 2014).*

Mahato et al., "Emerging Trends in Oral Delivery of Peptide and Protein Drugs," Critical Review in Therapeutic Drug Carrier Systems 20:153-214 (2003) (Year: 2003).*

Gupta et al, "Oral delivery of therapeutic proteins and peptides :a review on recent developments," Drug Delivery 20:237-246 (2013) (Year: 2013).*

International Search Report and Written Opinion mailed Feb. 26, 2020 in PCT Application No. PCT/IB2019/057637.

Valeria Cicatiello et al., "Powerful anti-tumor and anti-angiogenic activity of a new anti-vascular endothelial growth factor receptor 1 peptide in colorectal cancer models", Oncotarget, vol. 6, No. 12, Apr. 30, 2015 (Apr. 30, 2015), XP055589639, DOI: 10.18632/oncotarget.3384.

Salvatore Ponticelli, "New inhibitors of pathological angiogenesis", "Ph.D. Thesis", Jan. 1, 2007 (Jan. 1, 2007), XP055590024.

Salvatore Ponticelli et al., "Modulation of angiogenesis by a tetrameric tripeptide that antagonizes vascular endothelial growth factor receptor 1", Oct. 5, 2008 (Oct. 5, 2008), vol. 283, No. 49, pp. 34250-34259, XP002556278, DOI: 10.1074/JBC.M806607200, ISSN:0021-9258.

Andrea Caporale et al., "Synthetic Peptide Libraries. From Random Mixtures to In Vivo Testing", Current Medicinal Chemistry, vol. 25, Jul. 16, 2018 (Jul. 16, 2018), XP055589643, DOI: 10.2174/0929867325666180716110833, ISSN:0929-8673.

(Continued)

*Primary Examiner* — Julie Ha
*Assistant Examiner* — Kristina M Hellman
(74) *Attorney, Agent, or Firm* — Silvia Salvadori, P.C.; Silvia Salvadori

(57) ABSTRACT

The present invention relates to peptides, a composition comprising said peptides and the use thereof as inhibitors of angiogenesis and/or neoangiogenesis. Furthermore, the present invention relates to the use of said peptides and said composition for the treatment of pathologies correlated with an incorrect angiogenesis and/or neoangiogenesis. In particular, in this context reference is made to angiogenesis and/or neoangiogenesis correlated with VEGFR1.

5 Claims, 3 Drawing Sheets

Specification includes a Sequence Listing.

(56) References Cited

OTHER PUBLICATIONS

Qvit Nir et al., “Peptidomimetic therapeutics: scientific approaches and opportunities”, Drug Discovery Today, Elsevier, Amsterdam, NL, vol. 22, No. 2, Nov. 14, 2016 (Nov. 14, 2016), p. 454-462, XP029917037, DOI: 10.1016/J.DRUDIS.2016.11.003, ISSN: 1359-6446.

Fassina, G. et al., “Protein a Mimetic Peptide Ligand for Affinity Purification of Antibodies”, Journal of Molecular Recognition, Heyden & Son Ltd., London, GB, vol. 9, No. 5/06, Sep. 1, 1996 (Sep. 1, 1996), p. 564-569, XP002064544, DOI: 10.1002/(SICI)1099-1352(199634/12)9:5/6<564::AID-JMR302>3.0.CO;2-F, ISSN:0952-3499.

Rossella Di Stasi et al., “Peptides Interacting with Growth Factor Receptors Regulating Angiogenesis”, “Frontiers in Medicinal Chemistry”, p. 103-160, Mar. 20, 2016 (Mar. 20, 2016), Bentham Science Publishers, XP055648194, ISBN: 9781681082493.

Deming, “Funtional Modification of Thioether Groups in Peptides, Polypeptides, and Proteins”, ACS Publications, Bioconjugate Chemistry, vol. 28/Issue 3, Dec. 26, 2016, https://pubs.acs.org/doi/10.1021/acs.bioconjchem.6b00696 (Abstract), 1 pg.

Office Action dated Jul. 3, 2024 in U.S. Appl. No. 17/275,023, 21 pgs.

* cited by examiner

SEQUENCE LISTING

```
<160> NUMBER OF SEQ ID NOS: 4

<210> SEQ ID NO 1
<211> LENGTH: 7123
<212> TYPE: DNA
<213> ORGANISM: Artificial Sequence
<220> FEATURE:
<223> OTHER INFORMATION: VEGFR1 umano intero

<400> SEQUENCE: 1

atcgaggtcc gcgggaggct cggagcgcgc caggcggaca ctcctctcgg ctcctccccg      60

gcagcggcgg cggctcggag cgggctccgg ggctcgggtg cagcggccag cgggcgcctg     120

gcggcgagga ttacccgggg aagtggttgt ctcctggctg gagccgcgag acgggcgctc     180

agggcgcggg gccggcggcg gcgaacgaga ggacggactc tggcggccgg gtcgttggcc     240

gcggggagcg cgggcaccgg gcgagcaggc cgcgtcgcgc tcaccatggt cagctactgg     300

gacaccgggg tcctgctgtg cgcgctgctc agctgtctgc ttctcacagg atctagttca     360

ggttcaaaat taaaagatcc tgaactgagt ttaaaaggca cccagcacat catgcaagca     420

ggccagacac tgcatctcca atgcaggggg gaagcagccc ataaatggtc tttgcctgaa     480

atggtgagta aggaaagcga aaggctgagc ataactaaat ctgcctgtgg aagaaatggc     540

aaacaattct gcagtacttt aaccttgaac acagctcaag caaaccacac tggcttctac     600

agctgcaaat atctagctgt acctacttca aagaagaagg aaacagaatc tgcaatctat     660

atatttatta gtgatacagg tagacctttc gtagagatgt acagtgaaat ccccgaaatt     720

atacacatga ctgaaggaag ggagctcgtc attccctgcc gggttacgtc acctaacatc     780

actgttactt taaaaaagtt tccacttgac actttgatcc ctgatggaaa acgcataatc     840

tgggacagta gaaagggctt catcatatca aatgcaacgt acaaagaaat agggcttctg     900

acctgtgaag caacagtcaa tgggcatttg tataagacaa actatctcac acatcgacaa     960

accaatacaa tcatagatgt ccaaataagc acaccacgcc cagtcaaatt acttagaggc    1020
```

```
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tccctcgccg   1380
gaagttgtat ggttaaaaga tgggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc accccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agagatcagg aagcaccata cctcctgcga   2280
aacctcagtg atcacacagt ggccatcagc agttccacca ctttagactg tcatgctaat   2340
ggtgtccccg agcctcagat cacttggttt aaaaacaacc acaaaataca acaagagcct   2400
ggaattattt taggaccagg aagcagcacg ctgtttattg aaagagtcac agaagaggat   2460
gaaggtgtct atcactgcaa agccaccaac cagaagggct ctgtggaaag ttcagcatac   2520
ctcactgttc aaggaacctc ggacaagtct aatctggagc tgatcactct aacatgcacc   2580
tgtgtggctg cgactctctt ctggctccta ttaaccctct ttatccgaaa aatgaaaagg   2640
tcttcttctg aaataaagac tgactaccta tcaattataa tggacccaga tgaagttcct   2700
ttggatgagc agtgtgagcg gctcccttat gatgccagca agtgggagtt tgcccgggag   2760
agacttaaac tgggcaaatc acttggaaga ggggcttttg gaaaagtggt tcaagcatca   2820
gcatttggca ttaagaaatc acctacgtgc cggactgtgg ctgtgaaaat gctgaaagag   2880
ggggccacgg ccagcgagta caaagctctg atgactgagc taaaaatctt gacccacatt   2940
ggccaccatc tgaacgtggt taacctgctg ggagcctgca ccaagcaagg agggcctctg   3000
atggtgattg ttgaatactg caaatatgga aatctctcca actacctcaa gagcaaacgt   3060
gacttatttt ttctcaacaa ggatgcagca ctacacatgg agcctaagaa agaaaaaatg   3120
gagccaggcc tggaacaagg caagaaacca agactagata gcgtcaccag cagcgaaagc   3180
tttgcgagct ccggctttca ggaagataaa agtctgagtg atgttgagga agaggaggat   3240
tctgacggtt tctacaagga gcccatcact atggaagatc tgatttctta cagttttcaa   3300
gtggccagag gcatggagtt cctgtcttcc agaaagtgca ttcatcggga cctggcagcg   3360
```

-continued

```
agaaacattc ttttatctga gaacaacgtg gtgaagattt gtgattttgg ccttgcccgg   3420
gatatttata agaaccccga ttatgtgaga aaaggagata ctcgacttcc tctgaaatgg   3480
atggctcctg aatctatctt tgacaaaatc tacagcacca agagcgacgt gtggtcttac   3540
ggagtattgc tgtgggaaat cttctcctta ggtgggtctc catacccagg agtacaaatg   3600
gatgaggact tttgcagtcg cctgagggaa ggcatgagga tgagagctcc tgagtactct   3660
actcctgaaa tctatcagat catgctggac tgctggcaca gagacccaaa agaaaggcca   3720
agatttgcag aacttgtgga aaaactaggt gatttgcttc aagcaaatgt acaacaggat   3780
ggtaaagact acatcccaat caatgccata ctgacaggaa atagtgggtt tacatactca   3840
actcctgcct tctctgagga cttcttcaag gaaagtattt cagctccgaa gtttaattca   3900
ggaagctctg atgatgtcag atacgtaaat gctttcaagt tcatgagcct ggaaagaatc   3960
aaaacctttg aagaactttt accgaatgcc acctccatgt ttgatgacta ccagggcgac   4020
agcagcactc tgttggcctc tcccatgctg aagcgcttca cctggactga cagcaaaccc   4080
aaggcctcgc tcaagattga cttgagagta accagtaaaa gtaaggagtc ggggctgtct   4140
gatgtcagca ggcccagttt ctgccattcc agctgtgggc acgtcagcga aggcaagcgc   4200
aggttcacct acgaccacgc tgagctggaa aggaaaatcg cgtgctgctc cccgccccca   4260
gactacaact cggtggtcct gtactccacc ccacccatct agagtttgac acgaagcctt   4320
atttctagaa gcacatgtgt atttataccc ccaggaaact agcttttgcc agtattatgc   4380
atatataagt ttacaccttt atctttccat gggagccagc tgctttttgt gattttttta   4440
atagtgcttt tttttttttg actaacaaga atgtaactcc agatagagaa atagtgacaa   4500
gtgaagaaca ctactgctaa atcctcatgt tactcagtgt tagagaaatc cttcctaaac   4560
ccaatgactt ccctgctcca acccccgcca cctcagggca cgcaggacca gtttgattga   4620
ggagctgcac tgatcaccca atgcatcacg taccccactg ggccagccct gcagcccaaa   4680
acccagggca acaagcccgt tagccccagg gatcactggc tggcctgagc aacatctcgg   4740
gagtcctcta gcaggcctaa gacatgtgag gaggaaaagg aaaaaaagca aaaagcaagg   4800
gagaaaagag aaaccgggag aaggcatgag aaagaatttg agacgcacca tgtgggcacg   4860
gagggggacg gggctcagca atgccatttc agtggcttcc cagctctgac ccttctacat   4920
ttgagggccc agccaggagc agatggacag cgatgagggg acattttctg gattctggga   4980
ggcaagaaaa ggacaaatat ctttttttgga actaaagcaa attttagaac tttacctatg   5040
gaagtggttc tatgtccatt ctcattcgtg gcatgttttg atttgtagca ctgagggtgg   5100
cactcaactc tgagcccata cttttggctc ctctagtaag atgcactgaa aacttagcca   5160
gagttaggtt gtctccaggc catgatggcc ttacactgaa aatgtcacat tctattttgg   5220
gtattaatat atagtccaga cacttaactc aatttcttgg tattattctg ttttgcacag   5280
ttagttgtga aagaaagctg agaagaatga aaatgcagtc ctgaggagag gagttttctc   5340
catatcaaaa cgagggctga tggaggaaaa aggtcaataa ggtcaaggga aaaccccgtc   5400
tctataccaa ccaaaccaat tcaccaacac agttgggacc caaaacacag gaagtcagtc   5460
acgtttcctt ttcatttaat ggggattcca ctatctcaca ctaatctgaa aggatgtgga   5520
agagcattag ctggcgcata ttaagcactt taagctcctt gagtaaaaag gtggtatgta   5580
atttatgcaa ggtatttctc cagttgggac tcaggatatt agttaatgag ccatcactag   5640
aagaaaagcc cattttcaac tgctttgaaa cttgcctggg gtctgagcat gatgggaata   5700
gggagacagg gtaggaaagg gcgcctactc ttcagggtct aaagatcaag tgggccttgg   5760
```

```
atcgctaagc tggctctgtt tgatgctatt tatgcaagtt agggtctatg tatttatgat   5820

gtctgcacct tctgcagcca gtcagaagct ggagaggcaa cagtggattg ctgcttcttg   5880

gggagaagag tatgcttcct tttatccatg taatttaact gtagaacctg agctctaagt   5940

aaccgaagaa tgtatgcctc tgttcttatg tgccacatcc ttgtttaaag gctctctgta   6000

tgaagagatg ggaccgtcat cagcacattc cctagtgagc ctactggctc ctggcagcgg   6060

cttttgtgga agactcacta gccagaagag aggagtggga cagtcctctc caccaagatc   6120

taaatccaaa caaaagcagg ctagagccag aagagaggac aaatctttgt tcttcctctt   6180

ctttacatac gcaaaccacc tgtgacagct ggcaatttta taaatcaggt aactggaagg   6240

aggttaaaca cagaaaaaag aagacctcag tcaattctct acttttttt tttttccaa   6300

atcagataat agcccagcaa atagtgataa caaataaaac cttagctatt catgtcttga   6360

tttcaataat taattcttaa tcattaagag accataataa atactccttt tcaagagaaa   6420

agcaaaacca ttagaattgt tactcagctc cttcaaactc aggtttgtag catacatgag   6480

tccatccatc agtcaaagaa tggttccatc tggagtctta atgtagaaag aaaaatggag   6540

acttgtaata atgagctagt tacaaagtgc ttgttcatta aaatagcact gaaaattgaa   6600

acatgaatta actgataata ttccaatcat ttgccattta tgacaaaaat ggttggcact   6660

aacaaagaac gagcacttcc tttcagagtt tctgagataa tgtacgtgga acagtctggg   6720

tggaatgggg ctgaaaccat gtgcaagtct gtgtcttgtc agtccaagaa gtgacaccga   6780

gatgttaatt ttagggaccc gtgccttgtt tcctagccca caagaatgca aacatcaaac   6840

agatactcgc tagcctcatt taaattgatt aaaggaggag tgcatctttg gccgacagtg   6900

gtgtaactgt atgtgtgtgt gtgtgtgtgt gtgtgtgtgt gtgtgtgggt gtatgtgtgt   6960

tttgtgcata actatttaag gaaactggaa ttttaaagtt acttttatac aaaccaagaa   7020

tatatgctac agatataaga cagacatggt ttggtcctat atttctagtc atgatgaatg   7080

tattttgtat accatcttca tataataaac ttccaaaaac aca                     7123
```

```
<210> SEQ ID NO 2
<211> LENGTH: 1338
<212> TYPE: PRT
<213> ORGANISM: Artificial Sequence
<220> FEATURE:
<223> OTHER INFORMATION: VEGFR1 umano intero

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
```

-continued

```
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540
```

-continued

```
Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960
```

-continued

Thr Ser Ser Glu Ser Phe Ala Ser Ser Gly Phe Gln Glu Asp Lys Ser
965 970 975

Leu Ser Asp Val Glu Glu Glu Glu Asp Ser Asp Gly Phe Tyr Lys Glu
980 985 990

Pro Ile Thr Met Glu Asp Leu Ile Ser Tyr Ser Phe Gln Val Ala Arg
995 1000 1005

Gly Met Glu Phe Leu Ser Ser Arg Lys Cys Ile His Arg Asp Leu
1010 1015 1020

Ala Ala Arg Asn Ile Leu Leu Ser Glu Asn Asn Val Val Lys Ile
1025 1030 1035

Cys Asp Phe Gly Leu Ala Arg Asp Ile Tyr Lys Asn Pro Asp Tyr
1040 1045 1050

Val Arg Lys Gly Asp Thr Arg Leu Pro Leu Lys Trp Met Ala Pro
1055 1060 1065

Glu Ser Ile Phe Asp Lys Ile Tyr Ser Thr Lys Ser Asp Val Trp
1070 1075 1080

Ser Tyr Gly Val Leu Leu Trp Glu Ile Phe Ser Leu Gly Gly Ser
1085 1090 1095

Pro Tyr Pro Gly Val Gln Met Asp Glu Asp Phe Cys Ser Arg Leu
1100 1105 1110

Arg Glu Gly Met Arg Met Arg Ala Pro Glu Tyr Ser Thr Pro Glu
1115 1120 1125

Ile Tyr Gln Ile Met Leu Asp Cys Trp His Arg Asp Pro Lys Glu
1130 1135 1140

Arg Pro Arg Phe Ala Glu Leu Val Glu Lys Leu Gly Asp Leu Leu
1145 1150 1155

Gln Ala Asn Val Gln Gln Asp Gly Lys Asp Tyr Ile Pro Ile Asn
1160 1165 1170

Ala Ile Leu Thr Gly Asn Ser Gly Phe Thr Tyr Ser Thr Pro Ala
1175 1180 1185

Phe Ser Glu Asp Phe Phe Lys Glu Ser Ile Ser Ala Pro Lys Phe
1190 1195 1200

Asn Ser Gly Ser Ser Asp Asp Val Arg Tyr Val Asn Ala Phe Lys
1205 1210 1215

Phe Met Ser Leu Glu Arg Ile Lys Thr Phe Glu Glu Leu Leu Pro
1220 1225 1230

Asn Ala Thr Ser Met Phe Asp Asp Tyr Gln Gly Asp Ser Ser Thr
1235 1240 1245

Leu Leu Ala Ser Pro Met Leu Lys Arg Phe Thr Trp Thr Asp Ser
1250 1255 1260

Lys Pro Lys Ala Ser Leu Lys Ile Asp Leu Arg Val Thr Ser Lys
1265 1270 1275

Ser Lys Glu Ser Gly Leu Ser Asp Val Ser Arg Pro Ser Phe Cys
1280 1285 1290

His Ser Ser Cys Gly His Val Ser Glu Gly Lys Arg Arg Phe Thr
1295 1300 1305

Tyr Asp His Ala Glu Leu Glu Arg Lys Ile Ala Cys Cys Ser Pro
1310 1315 1320

Pro Pro Asp Tyr Asn Ser Val Val Leu Tyr Ser Thr Pro Pro Ile
1325 1330 1335

<210> SEQ ID NO 3
<211> LENGTH: 1626
<212> TYPE: DNA

-continued

```
<213> ORGANISM: Artificial Sequence
<220> FEATURE:
<223> OTHER INFORMATION: VEGFR1 umano solubile

<400> SEQUENCE: 3

atggtcagct actgggacac cggggtcctg ctgtgcgcgc tgctcagctg tctgcttctc     60

acaggatcta gttcaggttc aaaattaaaa gatcctgaac tgagtttaaa aggcacccag    120

cacatcatgc aagcaggcca gacactgcat ctccaatgca gggggggaagc agcccataaa    180

tggtctttgc ctgaaatggt gagtaaggaa agcgaaaggc tgagcataac taaatctgcc    240

tgtggaagaa atggcaaaca attctgcagt actttaacct tgaacacagc tcaagcaaac    300

cacactggct tctacagctg caaatatcta gctgtaccta cttcaaagaa gaaggaaaca    360

gaatctgcaa tctatatatt tattagtgat acaggtagac ctttcgtaga gatgtacagt    420

gaaatccccg aaattataca catgactgaa ggaagggagc tcgtcattcc ctgccgggtt    480

acgtcaccta acatcactgt tactttaaaa aagtttccac ttgacacttt gatccctgat    540

ggaaaacgca taatctggga cagtagaaag ggcttcatca tatcaaatgc aacgtacaaa    600

gaaatagggc ttctgacctg tgaagcaaca gtcaatgggc atttgtataa gacaaactat    660

ctcacacatc gacaaaccaa tacaatcata gatgtccaaa taagcacacc acgcccagtc    720

aaattactta gaggccatac tcttgtcctc aattgtactg ctaccactcc cttgaacacg    780

agagttcaaa tgacctggag ttaccctgat gaaaaaaata agagagcttc cgtaaggcga    840

cgaattgacc aaagcaattc ccatgccaac atattctaca gtgttcttac tattgacaaa    900

atgcagaaca aagacaaagg actttatact tgtcgtgtaa ggagtggacc atcattcaaa    960

tctgttaaca cctcagtgca tatatatgat aaagcattca tcactgtgaa acatcgaaaa   1020

cagcaggtgc ttgaaaccgt agctggcaag cggtcttacc ggctctctat gaaagtgaag   1080

gcatttccct cgccggaagt tgtatggtta aaagatgggt tacctgcgac tgagaaatct   1140

gctcgctatt tgactcgtgg ctactcgtta attatcaagg acgtaactga agaggatgca   1200

gggaattata caatcttgct gagcataaaa cagtcaaatg tgtttaaaaa cctcactgcc   1260

actctaattg tcaatgtgaa accccagatt tacgaaaagg ccgtgtcatc gtttccagac   1320

ccggctctct acccactggg cagcagacaa atcctgactt gtaccgcata tggtatccct   1380

caacctacaa tcaagtggtt ctggcacccc tgtaaccata atcattccga agcaaggtgt   1440

gacttttgtt ccaataatga agagtccttt atcctggatg ctgacagcaa catgggaaac   1500

agaattgaga gcatcactca gcgcatggca ataatagaag gaaagaataa gcttccacca   1560

gctaacagtt ctttcatgtt gccacctaca agcttctctt ccaactactt ccatttcctt   1620

ccgtga                                                              1626


<210> SEQ ID NO 4
<211> LENGTH: 541
<212> TYPE: PRT
<213> ORGANISM: Artificial Sequence
<220> FEATURE:
<223> OTHER INFORMATION: VEGFR1 umano solubile

<400> SEQUENCE: 4

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
```

-continued

```
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460
```

-continued

```
Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
        515                 520                 525

Pro Thr Ser Phe Ser Ser Asn Tyr Phe His Phe Leu Pro
    530                 535                 540
```

PEPTIDES AND MEDICAL USES THEREOF

CROSS-REFERENCE TO RELATED APPLICATIONS

This application is a national phase application of PCT/IB2019/057637, filed on Sep. 11, 2019, which claims the benefit of Italian Patent Application No. 102018000008507, filed Sep. 11, 2018, both of which are incorporated by reference herein in their entirety.

TECHNICAL FIELD

The present invention relates to peptides, a composition comprising said peptides and the use thereof as inhibitors of angiogenesis and/or neoangiogenesis. Furthermore, the present invention relates to the use of said peptides and said composition for the treatment of pathologies correlated with an incorrect angiogenesis and/or neoangiogenesis. In particular, in this context reference is made to angiogenesis and/or neoangiogenesis correlated with VEGFR1.

PRIOR ART

Given the considerable severity and wide spectrum of pathologies for which inhibition of the activation of VEGFR-1 may have application, it is conceivable that there will be a strong demand for synthetic compounds capable of binding VEGFR-1 and able to interfere in the interaction between the VEGF-A, PIGF, VEGF-B ligands and VEGF-A/PIGF heterodimer with VEGFR-1. In fact, advantageously, synthetic compounds are intrinsically free of contaminants of biological origin and they can also be produced at a considerably lower cost than biotherapeutics of recombinant origin.

With the aim of neutralizing ligands, many therapeutic approaches use monoclonal antibodies because they are molecules characterized by high specificity and affinity. However, synthetic molecules, too, have their advantages, because they are easier and more inexpensive to produce, more stable and more easily deliverable.

In this regard, Ponticelli et al. recently described, in 2008, a tetrameric tripeptide selected from a peptide library, in which a peptide chain with the formula (R-Glu)-(S-Cys(Bzl))-(S-Cha) was tetramerized on a "core" of three lysines (Tam, J. P. 1988. Proc. Natl. Acad. Sci. USA 85:5409-5413).

The tetrameric peptide has the following structure:

Formula (I)

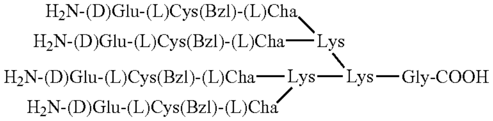

The scientific evidence reported by Ponticelli et al. demonstrates that the above-mentioned tetrameric peptide is capable of binding VEGFR1 and inhibiting, in vitro, the interaction of PIGF, VEGF-A and VEGF-B with an IC50 of about 10 μM. Furthermore, the peptide is not capable of binding VEGFR-2 and does not interfere in its activation by VEGF-A.

Finally, the peptide:

1) has shown anti-angiogenic activity in vitro, interfering with the pro-angiogenic activity of PIGF and VEGF-A;
2) is able to displace the VEGF-A-sFlt1 bond in the cornea-non-vascularized under physiological conditions-consequently rendering it VEGF-A free and capable of promoting neoangiogenesis;
3) when administered intraperitoneally, reduces tumor growth, angiogenesis and arteriogenesis as well as metastatization; and
4) when administered intravitreally, reduces choroidal neovascularization (Cicatiello et al. 2015).

The anti-angiogenic activity of the peptide is due both to an inhibition of the formation of new blood vessels and the capacity to inhibit the recruitment of inflammatory cells, preferably monocytes-macrophages, at the sites of neoangiogenesis.

The anti-arteriogenic activity is based on the capacity to inhibit the recruitment of smooth muscle cells at the sites of neoangiogenesis.

OBJECT OF THE INVENTION

In this context, the authors of the present invention have surprisingly found that by inserting, at the C-Terminal of the peptide, a chemical group, in particular an amino acid characterized by a side chain having a steric hindrance comparable to that of the thiol or thioether group, one significantly improves the activity of the molecule.

In fact, the above-mentioned modifications do not compromise selective binding with VEGFR1 and the capacity to compete, in a dose-dependent manner, with VEGF-A and/or PIGF in binding with VEGFR1. On the contrary, these modifications are capable of producing a 50% inhibition (IC50) of the interaction between PIGF or VEGF and VEGFR1 at a concentration of less than 1000 nM; this is a wholly unexpected result considering that the affinity of the peptide reported in Ponticelli et al. towards VEGFR1 is equal to 10000 nM or higher (expressed as IC50). In other words, the peptides of the present invention have an inhibitory capacity which is about one order of magnitude greater than that of the peptide reported in Ponticelli et al.

Furthermore, the authors of the present invention have surprisingly found that, when administered orally, or by gavage, both the peptide described in Ponticelli et al. and the peptides of the present invention have demonstrated a significant capacity to inhibit choroidal neovascularization. Therefore, these molecules are therapeutically effective for treating, preferably by oral administration, pathologies correlated with or in any case caused by an alteration of angiogenesis, preferably VEGFR1-dependent angiogenesis.

A detailed description of the invention follows, along with non-limiting illustrative examples which make reference to the figures and definitions below.

Figure 3:
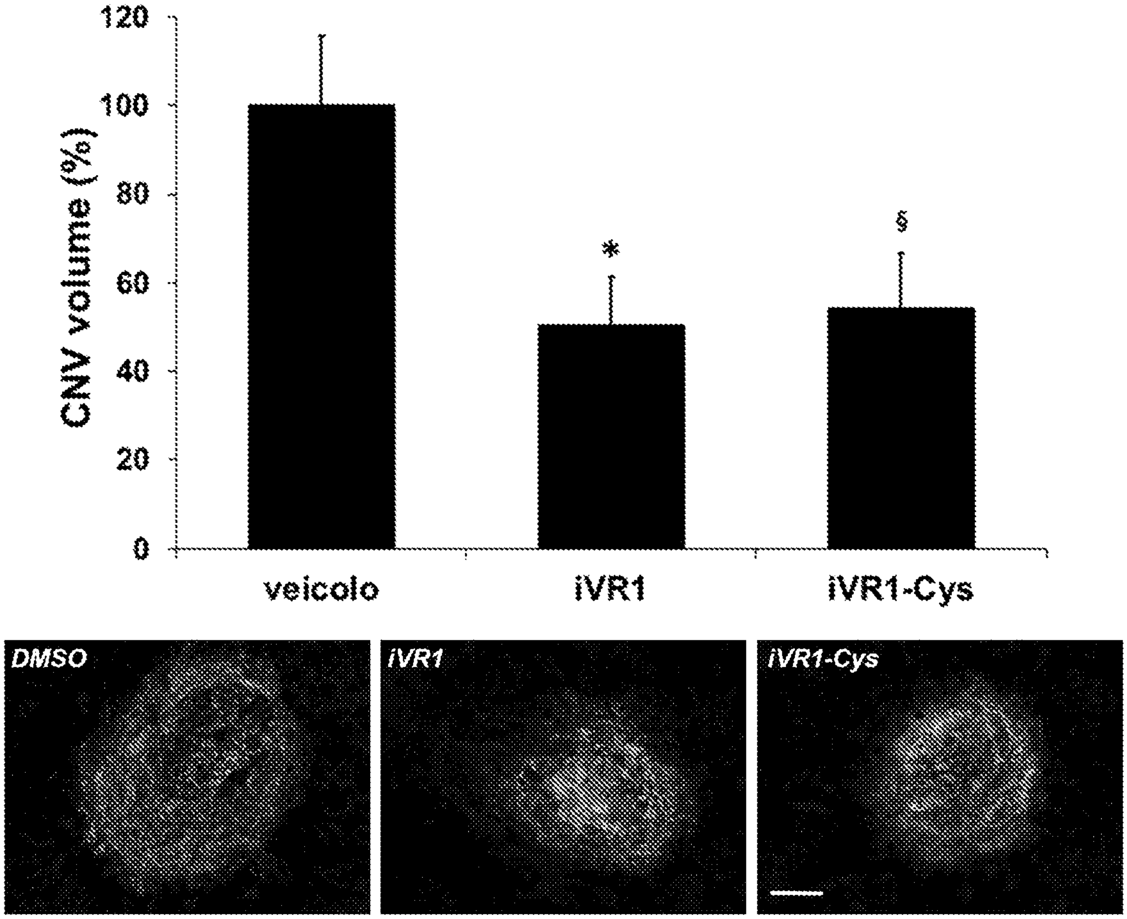

FIG. 3 shows that orally administered iVRI-Cys inhibits laser-induced choroidal neovascularization. Oral administration of iVR1-Cys at 50 mg/Kg twice a day for seven days brings about a 45.9% reduction of choroidal neovascularization, compared to the vehicle. The same amount of iVR1 brings about a similar inhibition of CNV (49.7%). Quantization of the volume of neovascularization was performed on n=18 spots for iVRI-Cys, n=20 spots for iVRI, and n=10 spots for the vehicle. The data are represented as the mean±SEM relative to the control. *p=0.001 and § p=0.007 vs DMSO. At the bottom, images representative of CNV. The bar represents 100 μm.

DEFINITIONS

In this context, the term "VEGF" means vascular endothelial growth factor. In humans there exist 5 different vascular endothelial growth factors, VEGF-A, VEGF-B, VEGF-C, VEGF-D and PIGF, encoded by five different genes. All are glycosylated dimeric proteins.

In this context, the term "VEGF-A" means vascular endothelial growth factor-A, formerly also known as VPF (vascular permeability factor). It is the most potent factor of the VEGF family, with a decisive role in both physiological and pathological angiogenesis. At least six different isoforms obtained by alternative splicing have been described in humans. All are capable of interacting with two receptors, which are called VEGFR-1 and VEGFR-2.

In this context, the term "PIGF" means placental growth factor, whose role is confined to the conditions of angiogenesis associated with pathological states. Four different isoforms have been described in humans. All are capable of specifically binding VEGFR-1. VEGF-A and PIGF act in strong synergism in pathological conditions, because both interact with VEGFR-1 and because when the two respective genes are expressed in the same cell, they are able to give rise to VEGF-A/PIGF heterodimers capable of interacting with VEGFR-1 or inducing VEGFR-1/VEGFR-2 heterodimerization.

In this context, the term "VEGFR-1" means VEGF receptor 1, also known as Flt-1. VEGFR-1 has an intracellular tyrosine-kinase domain, whilst the extracellular portion consists of seven IgG-like domains. VEGF-A, VEGF-B, or PIGF bring about dimerization of the receptor with a consequent activation by autophosphorylation of the tyrosine-kinase domains. Besides being expressed in endothelial cells, VEGFR-1 is expressed in many other types of cells, including smooth muscle cells, monocytes-macrophages, fibroblasts and endothelial precursors. It has a fundamental role in recruiting the different types of cells that contribute to angiogenesis. In this context, the term "soluble VEGFR-1" (sVEGFR-1) means the soluble form of VEGF receptor 1, also known as sFlt-1. It consists of the first six IgG-like extracellular domains of VEGFR-1 plus a tail and is generated from the VEGFR-1 gene by alternative splicing. It is normally expressed by the same cells in which the full-length form of VEGFR-1 is expressed, with the exception of the cornea, in which the soluble form is preferentially expressed, being decisive for maintaining the cornea in an avascular state. The messenger sequences of full-length and soluble human VEGFR1 are preferably SEQ ID NO: 1 and 2, respectively, whereas the protein sequences of full-length human VEGFR1 are SEQ ID NO: 3 and 4, respectively. Sequences characterized by an identity to the sequences described herein ranging from 80-99.9% must be considered part of the present description.

In this context, the term "VEGFR-2" means VEGF receptor 2, also known as KDR in humans and Flk-1 in mice. VEGFR-2 is specifically bound by VEGF-A, and has an organization in domains and an activation mechanism similar to the ones described for VEGFR-1. Unlike receptor 1, it is essentially expressed in endothelial cells. It has a fundamental role in stimulating the proliferation, migration and differentiation of endothelial cells.

In this context, the term "angiogenesis" means the process of formation of new blood vessels from pre-existing vessels; in this context angiogenesis is preferably referred to as a process of formation of new blood vessels associated with pathological conditions of various types, preferably selected from:

- neovascular eye diseases, preferably selected from: macular edema, the wet form of age-related macular degeneration, diabetic retinopathy, retinopathy of prematurity, retinopathy of central retinal vein occlusion, vitreous hemorrhage and retinal detachment and combinations thereof; and/or;
- solid tumors and/or tumor metastatization, said tumors preferably being selected from: leukemia and lymphomas, preferably acute lymphocytic leukemia, acute non-lymphocytic leukemia, chronic lymphocytic leukemia, multiple myeloma, Hodgkin's lymphoma, Hodgkin's disease, infantile or adult solid tumors, brain tumors, neuroblastoma, retinoblastoma, Wilms tumor, osteosarcomas and chondrosarcomas, lung tumors, colorectal cancer, breast cancer, prostate cancer, uterine cancer, ovarian cancer, urinary system cancer, bladder cancer, tumor of the oral cavity, tumor of the pancreas, melanoma and tumors of the skin, tumor of the stomach, tumor of the brain, tumor of the thyroid, tumor of the larynx, tumor of the liver, tumor of the testicles; and/or
- diseases of the bones or joints, preferably selected from: rheumatoid arthritis, synovitis, cartilage and/or bone destruction, osteomyelitis, hypertrophy and/or hyperplasia of the synovial tissue, formation of osteophytes, neoplasms and/or metastases and combinations thereof; and/or
- pathologies of blood vessels, preferably selected from: atherosclerosis, hemangioma, hemangioendothelioma and combinations thereof; and/or
- skin diseases, preferably selected from: psoriasis, warts, pyogenic granulomas, hair growth, Kaposi's sarcoma, keloids of wounds, allergic edema, neoplasms and combinations thereof; and/or
- angiogenesis observed in pathologies of adipose tissue, preferably obesity; and/or
- diabetes and/or its consequences, preferably retinopathy and/or diabetic foot; and/or
- diseases of hematopoiesis, preferably AIDS and/or Kaposi's sarcoma.

In this context, the term “neoangiogenesis” means new angiogenesis, preferably with reference to the formation of new blood vessels in tissues in which they were previously absent and/or an increase in the number of blood vessels in already vascularized tissues; in this context, the neo-angiogenesis is preferably dependent on the activity of VEGFR-1.

In this context, the term “vascularization” means angiogenesis, i.e., they are used as synonyms.

In this context, the term “neovascularization” means neoangiogenesis, preferably dependent on the activity of VEGFR-1.

In this context, the term “arteriogenesis” means the process of stabilization of new blood vessels through the covering of the vessels with smooth muscle cells.

In this context, “inhibitor” means a chemical and/or biological entity capable of antagonizing the activity of a receptor by binding the receptor itself and/or the soluble ligands thereof, thus preventing their interaction.

In this context, the term “effective dose” means a dosage interval within which the administration of the active substance described in the invention is capable of determining the desired biological effect. As is well known to the person skilled in the art, it may vary depending on: state of health, physical condition of the individual who needs to be treated, age, the formulation of the active substance, the assessment of the physician taking care of the patient, the ability of the system of the single individual to respond effectively, degree of response desired, taxonomic group (for example, human, non-human primate, primate, etc.), and other relevant factors. It is expected that the effective dose of the active substance described in the invention will fall within an interval that is sufficiently wide to be determined with routine tests. Generally, as reported by Ragan-Shaw et al. (FASEB J. 2008 March; 22 (3): 659-61), and thus in this context as well, the effective dose administered preferably ranges between 10 and 2000 mg/dose when administered preferably systemically, preferably systemically by the enteral route, more preferably orally, sublingually or rectally. Alternatively, the effective dose administered ranges between 1 and 100 mg/dose when administered preferably intravitreally. Alternatively, the effective dose administered preferably ranges between 0.16 and 33.3 mg/kg of body weight. The treatment program provides for a single dose or multiple doses.

DETAILED DESCRIPTION OF PREFERRED EMBODIMENTS OF THE INVENTION

A first aspect of the invention refers to peptides, preferably multimeric peptides, isolated and characterized by the following general formula (II):

{{{[Y1-Glu-Cys(Bzl)-Cha]2-Z1}*i*-Z2}*j*-Z3}*z*-Y2-Y3 (Formula II)

wherein $Y^1$ is the amino-terminal function of the peptide ($NH_2$) or at least one chemical group preferably selected in Table I. The list is understood also to include chemical groups, preferably amino acids, which possess a steric hindrance and/or chemical properties, in particular a side chain in the case of amino acids, which mimic those of the chemical groups, preferably the amino acids, listed in Table I and/or which are characterized by a similarity, preferably of at least 70%, said similarity being determined with methods known to the person skilled in the art, for example, but not exclusively, with the methods described in Woong-Hee Shin et al., Molecules 2015, 20, 12841-12862.

In this context, it should be clarified that the D/L notations suitable for defining the absolute configuration of the chiral centers present in the groups of the present description are interchangeable with the R/S notation following rules reported in the literature, as is known to the person skilled in the art.

TABLE I

| N. | 3-letter code | Abbreviation |
|---|---|---|
| 1 | D-Alanine | D-Ala |
| 2 | D-Aspartic Acid | D-Asp |
| 3 | D-Valine | D-Val |
| 4 | D-Glutamic Acid | D-Glu |
| 5 | L-Cyclohexylalanine | L-Cha |
| 6 | D-Phenylalanine | D-Phe |
| 7 | D-Threonine | D-Thr |
| 8 | D-Methionine | D-Met |
| 9 | D-Lysine | D-Lys |
| 10 | D-Cysteine(S-acetamidomethyl) | D-Cys(Acm) |
| 11 | D-Tyrosine | D-Tyr |
| 12 | D-Proline | D-Pro |
| 13 | D-Leucine | D-Leu |
| 14 | D-Arginine | D-Arg |
| 15 | D-Asparagine | D-Asn |
| 16 | D-Isoleucine | D-Ile |
| 17 | D-Arginine($N^f$-Tosyl) | D-Arg(Tos) |
| 18 | D-Serine | D-Ser |
| 19 | L-Cysteine(S-benzyl) | L-Cys(Bzl) |
| 20 | L-Cysteine(S-acetamidomethyl) | L-Cys(Acm) |
| 21 | D-Histidine | D-His |
| 22 | D-Glutamine | D-Gln |
| 23 | D-Tryptophan | D-Trp |
| 24 | L-Glutamic-(β-allyl) Acid | L-Glu(β-OAll) |
| 25 | β-Alanine | β-Ala |
| 26 | L-Cysteine(S-p-methyl-benzyl) | L-Cys(p-MeBzl) |
| 27 | L-Cysteine(S-tert-butyl) | L-Cys(tBu) |
| 28 | L-Methionine-sulfone | L-Met(O)2 |
| 29 | L-Methionine-sulfoxide | L-Met(O) |
| 30 | Glycine | Gly |

Glu indicates glutamic acid, preferably in an absolute configuration R on the Cα of the amino acid (R-Glu).

Cys(Bzl) indicates benzyl cysteine, preferably in an absolute configuration S on the Cα of the amino acid containing a sulfur-linked benzyl group of the amino acid (S-benzyl-cysteine/S-Cys(Bzl) side chain.

Cha indicates cyclohexylalanine, preferably in an absolute configuration S on the Cα of the amino acid (S-cyclohexylalanine/S-Cha).

Y2 is preferably selected from:

1. the tripeptide R-Glu-S-Cys(Bzl)-S-Cha, and an α-amino acid, preferably selected from a glycine or an α-amino acid characterized by at least one thiol or thioether group, said α-amino acid characterized by at least one thiol or thioether group preferably being selected from the ones shown in Table II and combinations thereof.

The list is understood also to include chemical groups, preferably amino acids, which possess a steric hindrance and/or chemical properties, in particular a side chain in the case of amino acids, which mimic those of the chemical groups, preferably the amino acids, listed in Table II and which are characterized by a similarity, preferably of at least 70%, said similarity being determined with methods known to the person skilled in the art, for example, but not exclusively, with the methods described in Woong-Hee Shin et al., Molecules 2015, 20, 12841-12862.

TABLE II

| N. | Y |
|---|---|
| 1 | D-cysteine |
| 2 | L-cysteine |
| 3 | L-homocysteine |
| 4 | D-homocysteine |
| 5 | D-cysteine-S-methyl |
| 6 | L-cysteine-S-methyl |
| 7 | D-cysteine-S-ethyl |
| 8 | L-cysteine-S-ethyl |
| 9 | L-methionine |
| 10 | D-methionine |
| 11 | D-cysteine-S-benzyl |
| 12 | L-cysteine-S-benzyl |
| 13 | L-methionine sulfoxide |
| 14 | D-methionine sulfoxide |
| 15 | L-methionine sulfone |
| 16 | D-methionine sulfone |
| 17 | D-serine |
| 18 | L-serine |
| 19 | D- serine -O-methyl |
| 20 | L- serine -O-methyl |
| 21 | D- serine -O-ethyl |
| 22 | L- serine -O-ethyl |
| 23 | D- serine -O-benzyl |
| 24 | L- serine -O-benzyl |
| 25 | D-threonine |
| 26 | L- threonine |
| 27 | D- threonine -O-methyl |
| 28 | L- threonine -O-methyl |
| 29 | D threonine -O-ethyl |
| 30 | L- threonine -O-ethyl |
| 31 | D- threonine -O-benzyl |
| 32 | L- threonine -O-benzyl |

Y3 is preferably selected from: a carboxylic group, a carboxyamide group, an N-methyl-substituted carboxyamide or di-substituted N, N-dimethyl group, a hydroxyl group and a hydrogen.

Z1, Z2 and Z3 preferably indicate a trifunctional group, preferably characterized by the following formula (III):

(III)

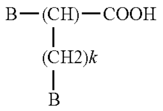

where k is an integer, preferably comprised between 1 and 4, and B is preferably an amino group or a hydroxyl group. Said trifunctional molecule is preferably in an R or S absolute configuration.

Preferably, Z1, Z2 and Z3 are used for the purpose of obtaining a branched structure. In fact, this type of structure is generally used to multimerize peptides following known methods for this purpose, for example when B is an amino group, the method described by Tam et al. can be used (Tam J. P., 1988, PNAS, 85, 5409-5413).

Z1, Z2 and Z3 can be assembled in such a way as to obtain a structure of formula (II) with multiple groups Z1, Z2 and Z3, preferably containing 1, 3 or 7 trifunctional molecules.

According to a preferred embodiment of the invention, Z1 and/or Z2 and/or Z3 are joined to one another preferably by amide bonds in such a way as to form a branched structure. Alternatively, they can be joined to one another by an ester bond, for example when B is preferably a hydroxyl group.

i is preferably 4, 2 or 1.

j is preferably 2, 1 or 0.

z is preferably 1 or 0.

According to a preferred embodiment, when i=4, j=2 and z=1. According to a further preferred embodiment, when i=2, j=1 and z=0.

According to a further preferred embodiment, when i=1, j=z=0.

If j=0 the Z2 group is omitted and if z=0 the Z3 group is omitted.

For the purposes of the present invention, the particularly preferred embodiment envisages that i is equal to 2, j is equal to 1 and Z2 is 0 or omitted (in other words, Z3 is not present, i.e., it is absent).

In the particularly preferred embodiment of the invention, Z1, Z2 and Z3 are a R- or S-lysine (k=4) and i is preferably equal to 2.

The preferred formula of the multimeric peptide of the invention is represented by the formula below (Figure IIa):

(FIG. IIa)

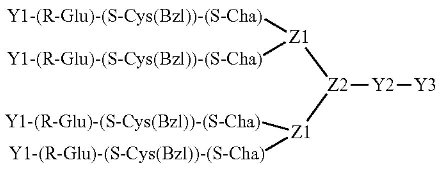

According to a particularly preferred embodiment of the invention, the peptide is a tetrameric peptide characterized by the formula (IIb):

(Formula IIb)

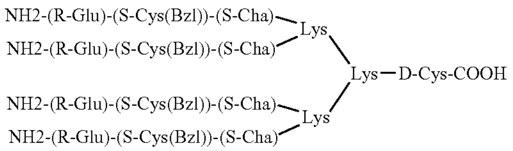

In which:

Y1 is a hydrogen atom;

Y2 is a D-cysteine;

Y3 is an unsubstituted primary amide group

Z1, Z2 and Z3 being as defined above;

i equal to 2;

j equal to 1; and z equal to zero, i.e., absent.

For the sake of convenience, the particularly preferred embodiment of the peptide characterized by the formula IIb will be called iVR1-Cys from this moment on.

The above-described peptides show a biological activity, preferably a modulation activity, more preferably an activity of inhibiting angiogenesis and/or neoangiogenesis, which is improved compared to that of the peptide described by Ponticelli et al. as reported and discussed below in the experimental results which—in this context—have a non-limiting illustrative purpose. The angiogenesis and/or neoangiogenesis being referred to in this context is preferably VEGFR1-dependent as earlier defined.

The peptide described in Ponticelli et al. is also a tetrameric peptide characterized by the formula (IIc):

(Formula IIc)

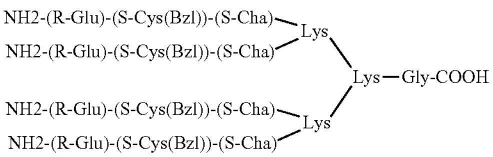

Wherein:

Y1 is a hydrogen atom;

Y2 is a glycine;

Y3 is an unsubstituted primary amide group

Z1, Z2 and Z3 being as defined above;

i equal to 2;

j equal to 1; and z equal to zero.

For the sake of convenience, the particularly preferred embodiment of the peptide characterized by the formula IIc will be called iVR1 from this moment on.

The authors of the present invention have surprisingly found that by modifying IVR1, in particular at the terminal carboxyl, preferably by inserting an R-Glu-S-Cys(Bzl)-S-Cha group or an α-amino acid, preferably selected from an α-amino acid characterized by at least one thiol or thioether group, said α-amino acid characterized by at least one thiol or thioether group preferably being selected from the ones shown in Table II and combinations thereof, one obtains peptides characterized by an improved biological activity, preferably an improved modulation capacity, preferably by inhibiting angiogenesis and/or neoangiogenesis as defined above.

In fact, as shown and discussed in greater detail in the examples, iVR1-Cys has demonstrated a capacity to inhibit, in a dose-dependent manner, the interaction of both PIGF and VEGF-A with VEGFR-1, a capacity which is improved compared to iVR1. In particular, the concentration at which iVR1-Cys is capable of inhibiting the interaction of PIGF with VEGFR-1 by 50% (IC50) is below 1000 nM, whereas the IC50 for VEGF-A/VEGFR-1 inhibition is close to or just above 1000 nM. iVR1, on the other hand, is capable of inhibiting the interaction of PIGF with VEGFR-1 by 50% (IC50) at a concentration close to 10000 nM. Similarly, the IC50 for VEGF-A/VEGFR-1 inhibition by iVR1 is close to or just above 10000 nM.

Therefore, iVR1-Cys shows an inhibitory capacity that is 10 times greater than the one reported for iVR1.

Furthermore, the authors have demonstrated—with in vivo assays—that iVR1 brings about a 37.8% and 39.3% inhibition of choroidal neovascularization vs the vehicle and PC ($p<0.05$), whereas iVR1-Cys brings about a 48.9% and 51.0% inhibition vs the vehicle and PC ($p<0.02$). Therefore, iVR1-Cys shows a greater inhibition effectiveness than the peptide iVR1, as it brings about a further 19.3% reduction of neovascularization.

Finally, when administered orally, or by gavage, both peptides tested by way of example are capable of inducing a significant inhibition of neovascularization compared to the vehicle.

The latter fact is particularly relevant because although Ponticelli et al. and Cicatiello et al. 2015 had already demonstrated the capacity of iVR1 to inhibit choroidal angiogenesis and neovascularization by intravitreal injection, it was absolutely not expected that administering the peptides through different routes, in particular by gavage, could maintain or even improve the therapeutic effectiveness, above all in the case of a highly complex organ like the eye and pathologies affecting it caused by or in any case correlated with an unregulated, preferably increased angiogenesis/neoangiogenesis. In particular, the neovascular diseases of the eye to which reference is being made are preferably selected from: macular edema, the wet form of age-related macular degeneration, diabetic retinopathy, retinopathy of prematurity, central retinal vein occlusion, vitreous hemorrhage and retinal detachment and combinations thereof.

In the light of this evidence, it is clear that the administration of the peptides of the invention through the oral route, or by gavage, is therapeutically effective also for treating pathologies, such as cancer for example, which are in general correlated with angiogenesis/neoangiogenesis. The angiogenesis or neoangiogenesis to which reference is being made is preferably VEGFR1-dependent.

According to one embodiment of the invention, the peptides can be modified in order to facilitate or improve delivery, preferably by PEGylation, or using container/shuttle/carrier systems, preferably liposomes, micelles, capsules, emulsions, matrices, gels and the like.

A further aspect of the present invention relates to a composition comprising the peptides as described in detail and at least one further pharmaceutically accepted ingredient.

The composition preferably comprises at least one peptide characterized by Formula IIa, more preferably the peptide characterized by Formula IIb, i.e., iVR1-Cys.

In this context, pharmaceutically accepted ingredient means a compound selected from: excipients, diluents, carriers, adjuvants, preservatives, antibiotics, anti-inflammatoireils, vitamins, antioxidants, chelating agents, solubilizing agents, viscosity agents, inert gases, surfactant agents, emulsifying agents, buffer substances, immunosuppressants, anti-tumor agents and combinations thereof.

For example, according to one embodiment, the composition comprises the peptides of the invention in combination with: at least one anti-angiogenic/anti-neoangiogenic molecule, an antibody neutralizing the action of PIGF, at least one anti-VEGFR-1, anti-VEGFR-2, anti-VEGFR-3 antibody, at least one anti-VEGF-A, anti-VEGF-B, anti-VEGF-C, anti-VEGF-D, anti-VEGF-E antibody and combinations thereof.

A further aspect of the present invention relates to the peptides as described above, preferably a peptide characterized by Formula IIa, more preferably the peptide characterized by Formula IIb, i.e., iVR1-Cys, for use as a medicament.

A further aspect of the present invention relates to the peptides as described above, preferably a peptide characterized by Formula IIa, more preferably the peptide characterized by Formula IIb, i.e., iVR1-Cys, or the composition comprising said peptides as described above for use in the treatment of a pathological condition associated with or caused by incorrect angiogenesis/neo-angiogenesis, i.e., a pathology in which angiogenesis/neoangiogenesis is unregulated; it has preferably increased and therefore needs to be inhibited.

Besides being useful in the treatment of said pathologies, the peptides as described above, preferably a peptide characterized by Formula IIa, more preferably the peptide characterized by Formula IIb, i.e., iVR1-Cys, or the composition comprising said peptides as described above can also be used for the follow-up of further alternative therapeutic treatments for said pathologies.

As already said previously, the angiogenesis/neoangiogenesis, as earlier defined, is/are preferably dependent on/induced by/regulated by VEGFR1, or by the VEGFR1 pathway.

Said pathology/condition is preferably selected from:

- neovascular eye diseases, preferably selected from: macular edema, the wet form of age-related macular degeneration, diabetic retinopathy, retinopathy of prematurity, retinopathy of central retinal vein occlusion, vitreous hemorrhage and retinal detachment and combinations thereof; and/or
- solid or liquid tumors and/or tumor metastasis, said tumors preferably being selected from: leukemias and lymphomas, preferably acute lymphocytic leukemia, acute non-lymphocytic leukemia, chronic lymphocytic leukemia, multiple myeloma, Hodgkin's lymphoma, Hodgkin's disease, infantile or adult solid tumors, brain tumors, neuroblastoma, retinoblastoma, Wilms tumor, osteosarcomas and chondrosarcomas, lung tumors, colorectal cancer, breast cancer, prostate cancer, uterine cancer, ovarian cancer, urinary system cancer, bladder cancer, tumor of the oral cavity, tumor of the pancreas, melanoma and tumors of the skin, tumor of the stomach, tumor of the brain, tumor of the thyroid, tumor of the larynx, tumor of the liver, tumor of the testicles; and/or
- diseases of the bones or joints, preferably selected from: rheumatoid arthritis, synovitis, cartilage and/or bone destruction, osteomyelitis, hypertrophy and/or hyperplasia of the synovial tissue, formation of osteophytes, neoplasms and/or metastases and combinations thereof; and/or
- pathologies of blood vessels, preferably selected from: atherosclerosis, hemangioma, hemangioendothelioma and combinations thereof; and/or
- skin diseases, preferably selected from: psoriasis, warts, pyogenic granulomas, hair growth, Kaposi's sarcoma, keloids of wounds, allergic edema, neoplasms and combinations thereof; and/or
- angiogenesis observed in pathologies of adipose tissue, preferably obesity; and/or
- diabetes and/or its consequences, preferably retinopathy and/or diabetic foot; and/or
- diseases of hematopoiesis, preferably AIDS and/or Kaposi's sarcoma.

For the above-described medical purposes, the peptides and the composition of the invention can optionally be combined or also used before or after already known drugs used to treat the above pathologies.

Furthermore, the peptides or the composition of the invention can be associated with already known treatments of a surgical, radiotherapeutic or chemotherapeutic type which are used to treat the above pathologies.

The peptides of the present invention or the composition comprising said peptides as described above can be formulated so as to be administered through any route. The route of administration is preferably selected from: systemic route, preferably the oral route, gavage, sublingual or rectal route, the topical, subcutaneous, intramuscular, intravenous, intra-arterial, intraperitoneal, intradermal and intraepidermal route.

The peptides or the composition of the invention can be formulated as a solid, for example as pills, tablets, granules, soluble granules, pellets, beads, lozenges, and the like. Alternatively, the peptides or the composition of the invention can be formulated as a liquid solution, for example to be administered by injection, inhalation or nebulization, or as drops or sprays.

The peptides of the present invention or the composition comprising said peptides as described above can be administered as a bolus.

The peptides of the present invention or the composition comprising said peptides as described above can be administered by means of medical devices, for example by means of stents, pump or patches.

The administration can preferably be continuous, by controlled release or by constant release, preferably using devices for ocular drug delivery.

Administration by the oral route or gavage is particularly preferred. In fact, as previously described, the peptides of the present invention, iVR1 included, show to be effective in inhibiting angiogenesis/neoangiogenesis also when administered by gavage. They have shown to be effective also for inhibiting angiogenesis/neoangiogenesis in the eye; in other words, when the peptides of the invention, iVR1 included, were administered by gavage, an inhibition of angiogenesis/neoangiogenesis in the eye was surprisingly observed. The angiogenesis/neoangiogenesis being referred to is preferably VEGFR1-dependent.

In the light of this scientific evidence, a further aspect of the present invention relates to the peptides of the invention, preferably at least one peptide characterized by FIG. 11*a*, more preferably the peptide characterized by Formula IIb, i.e., iVR1-Cys, and/or the peptide characterized by Formula IIc, i.e., iVR1, or a composition comprising said peptides administered orally or by gavage, for use in the treatment of pathologies caused by or in any case associated with an incorrect, preferably increased, angiogenesis/neoangiogenesis, preferably VEGFR1-dependent.

Said pathology/condition is preferably selected from:

- neovascular eye diseases, preferably selected from: macular edema, the wet form of age-related macular degeneration, diabetic retinopathy, retinopathy of prematurity, retinopathy of central retinal vein occlusion, vitreous hemorrhage and retinal detachment and combinations thereof; and/or
- solid tumors and/or tumor metastasis, said tumors preferably being selected from: leukemias and lymphomas, preferably acute lymphocytic leukemia, acute non-lymphocytic leukemia, chronic lymphocytic leukemia, multiple myeloma, Hodgkin's lymphoma, Hodgkin's disease, infantile or adult solid tumors, brain tumors, neuroblastoma, retinoblastoma, Wilms tumor, osteosarcomas and chondrosarcomas, lung tumors, colorectal cancer, breast cancer, prostate cancer, uterine cancer, ovarian cancer, urinary system cancer, bladder cancer, tumor of the oral cavity, tumor of the pancreas, melanoma and tumors of the skin, tumor of the stomach, tumor of the brain, tumor of the thyroid, tumor of the larynx, tumor of the liver, tumor of the testicles; and/or
- diseases of the bones or joints, preferably selected from: rheumatoid arthritis, synovitis, cartilage and/or bone destruction, osteomyelitis, hypertrophy and/or hyperplasia of the synovial tissue, formation of osteophytes, neoplasms and/or metastases and combinations thereof; and/or
- pathologies of blood vessels, preferably selected from: atherosclerosis, hemangioma, hemangioendothelioma and combinations thereof; and/or
- skin diseases, preferably selected from: psoriasis, warts, pyogenic granulomas, hair growth, Kaposi's sarcoma, keloids of wounds, allergic edema, neoplasms and combinations thereof; and/or angiogenesis observed in pathologies of adipose tissue, preferably obesity; and/or diabetes and/or its consequences, preferably retinopathy and/or diabetic foot; and/or diseases of hematopoiesis, preferably AIDS and/or Kaposi's sarcoma.

The peptide or the composition of the invention is administered to any animal that has need of it, preferably an animal in which there is a need to inhibit VEGFR-1-dependent neoangiogenesis.

Said animal is preferably a mammal, more preferably it is a human being.

The effective dose of the peptide or of the composition as described above that is administered preferably ranges:

between 10 and 2000 mg/dose, preferably when administered systemically, preferably by the systemic enteral route, more preferably orally, sublingually or rectally; or between 1 and 100 mg/dose when administered preferably intravitreally. Alternatively, the effective dose that is administered preferably ranges between 0.16 and 33.3 mg/kg of body weight.

The treatment program preferably provides for a single dose or multiple doses.

The sequences of the invention are annotated according to the international standard WIPO ST.25 and the description thereof was developed with the program Patent-In 3.5. A description of the sequences is attached hereto.

In the present invention, the sequences identified in Table III and the sequences having an identity ranging from 80 to 99.9% are to be considered described.

TABLE III

| Sequence | Name | SEQ ID |
|---|---|---|
| atcgaggtcc gcgggaggct cggagcgcgc caggcggaca ctcctctcgg<br>ctcctccccg gcagcggcgg cggctcggag cgggctccgg ggctcgggtg<br>cagcggccag cgggcgcctg gcggcgagga ttacccgggg aagtggttgt<br>ctcctggctg gagccgcgag acgggcgctc agggcgcggg gccggcggcg<br>gcgaacgaga ggacggactc tggcggccgg gtcgttggcc gcggggagcg<br>cgggcaccgg gcgagcaggc cgcgtcgcgc tcaccatggt cagctactgg<br>gacaccgggg tcctgctgtg cgcgctgctc agctgtctgc ttctcacagg atctagttca<br>ggttcaaaat taaaagatcc tgaactgagt ttaaaaggca cccagcacat<br>catgcaagca ggccagacac tgcatcttcca atgcaggggg ggaagcagccc<br>ataaatggtc tttgcctgaa atggtgagta aggaaagcga aaggctgagc<br>ataactaaat ctgcctgtgg aagaaatggc aaacaattct gcagtacttt aaccttgaac<br>acagctcaag caaaccacac tggcttctac agctgcaaat atctagctgt acctacttca<br>aagaagaagg aaacagaatc tgcaatctat atatttatta gtgatacagg tagacctttc<br>gtagagatgt acagtgaaat ccccgaaattt atacacatga ctgaaggaag<br>ggagctcgtc attcccctgcc gggttacgtc acctaacatc actgttactt taaaaaagtt<br>tccacttgac actttgatcc ctgatggaaa acgcataatc tgggacagta gaaagggctt<br>catcatatca aatgcaacgt acaaagaaat agggcttctg acctgtgaag<br>caacagtcaa tgggcatttg tataagacaa actatctcac acatcgacaa<br>accaatacaa tcatagatgt ccaaataagc acaccacgcc cagtcaaatt<br>acttagaggc catactcttg tcctcaattg tactgctacc actcccttga acacgagagt<br>tcaaatgacc tggagttacc ctgatgaaaa aaataagaga gcttccgtaa<br>ggcgacgaat tgaccaaagc aattcccatg ccaacatatt ctacagtgtt cttactattg<br>acaaaatgca gaacaaagac aaaggacttt atacttgtcg tgtaaggagt<br>ggaccatcat tcaaatctgt taacacctca gtgcatatat atgataaagc attcatcact<br>gtgaaacatc gaaaacagca ggtgcttgaa accgtagctg gcaagcggtc<br>ttaccggctc tctatgaaag tgaaggcatt tccctcgccg gaagttgtat ggttaaaaga<br>tgggttacct gcgactgaga aatctgctcg ctatttgact cgtggctact cgttaattat<br>caaggacgta actgaagagg atgcagggaa ttatacaatc ttgctgagca<br>taaaacagtc aaatgtgttt aaaaacctca ctgccactct aattgtcaat gtgaaacccc<br>agatttacga aaaggccgtg tcatcgtttc cagacccggc tctctaccca ctgggcagca<br>gacaaatcct gacttgtacc gcatatggta tccctcaacc tacaatcaag tggttcttggc<br>accctgtaa ccataatcat tccgaagcaa ggtgtgactt ttgttccaat aatgaagagt<br>cctttatcct ggatgctgac agcaacatgg gaaacagaat tgagagcatc<br>actcagcgca tggcaataat agaaggaaag aataagatgg ctagcacctt<br>ggttgtggct gactctagaa tttctggaat ctacatttgc atagcttcca ataaagttgg<br>gactgtggga agaaacataa gccttttatat cacagatgtg ccaaatgggt ttcatgttaa<br>cttggaaaaa atgccgacgg aaggagagga cctgaaactg tcttgcacag<br>ttaacaagttt cttatacaga gacgttactt ggattttact gcggacagtt aataacagaa<br>caatgcacta cagtattagc aagcaaaaaa tggccatcac taaggagcac<br>tccatcactc ttaatcttac catcatgaat gtttccctgc aagattcagg cacctatgcc<br>tgcagagcca ggaatgtata cacaggggaa gaaatcctcc agaagaaaga<br>aattacaatc agagatcagg aagcaccata cctcctgcga aacctcagtg<br>atcacacagt ggccatcagc agttccacca ctttagactg tcatgctaat ggtgtccccg<br>agcctcagat cacttggttt aaaaacaacc acaaaataca acaagagcct<br>ggaattattt taggaccagg aagcagcacg ctgtttattg aaagagtcac<br>agaagaggat gaaggtgtct atcactgcaa agccaccaac cagaagggct<br>ctgtggaaag ttcagcatac ctcactgttc aaggaacct ggacaagtct aatctggagc<br>tgatcactct aacatgcacc tgtgtggctg cgactctctt ctggctccta ttaaccctct<br>ttatccgaaa aatgaaaagg tcttcttctg aaataaagac tgactaccta tcaattataa<br>tggacccaga tgaagttcct ttggatgagc agtgtgagcg gctcccttat gatgccagca<br>agtgggagtt tgcccgggag agacttaaac tgggcaaatc acttggaaga<br>ggggcttttg gaaaagtggt tcaagcatca gcatttggca ttaagaaatc acctacgtgc<br>cggactgtgg ctgtgaaaat gctgaaagag ggggccacgg ccagcgagta<br>caaagctctg atgactgagc taaaaatctt gacccacatt ggccaccatc tgaacgtggt<br>taacctgctg ggagcctgca ccaagcaagg agggcctctg atggtgattg<br>ttgaatactg caaatatgga aatctctcca actacctcaa gagcaaacgt gacttatttt | Full-length human VEGFR1 mRNA | SEQ ID NO: 1 |

TABLE III-continued

| Sequence | Name | SEQ ID |
|---|---|---|
| ttctcaacaa ggatgcagca ctacacatgg agcctaagaa agaaaaaatg | | |
| gagccaggcc tggaacaagg caagaaacca agactagata gcgtcaccag | | |
| cagcgaaagc tttgcgagct ccggctttca ggaagataaa agtctgagtg | | |
| atgttgagga agaggaggat tctgacggtt tctacaagga gcccatcact | | |
| atggaagatc tgatttctta cagttttcaa gtggccagag gcatggagtt cctgtcttcc | | |
| agaaagtgca ttcatcggga cctggcagcg agaaacattc ttttatctga | | |
| gaacaacgtg gtgaagattt gtgattttgg ccttgcccgg gatatttata agaaccccga | | |
| ttatgtgaga aaaggagata ctcgacttcc tctgaaatgg atggctcctg aatctatctt | | |
| tgacaaaatc tacagcacca agagcgacgt gtggtcttac ggagtattgc | | |
| tgtgggaaat cttctcctta ggtgggtctc catacccagg agtacaaatg gatgaggact | | |
| tttgcagtcg cctgagggaa ggcatgagga tgagagctcc tgagtactct | | |
| actcctgaaa tctatcagat catgctggac tgctggcaca gagacccaaa | | |
| agaaaggcca agatttgcag aacttgtgga aaaactaggt gatttgcttc | | |
| aagcaaatgt acaacaggat ggtaaagact acatcccaat caatgccata | | |
| ctgacaggaa atagtgggtt tacatactca actcctgcct tctctgagga cttcttcaag | | |
| gaaagtattt cagctccgaa gtttaattca ggaagctctg atgatgtcag atacgtaaat | | |
| gctttcaagt tcatgagcct ggaaagaatc aaaacctttg aagaactttt accgaatgcc | | |
| acctccatgt ttgatgacta ccagggcgac agcagcactc tgttggcctc tcccatgctg | | |
| aagcgcttca cctggactga cagcaaaccc aaggcctcgc tcaagattga | | |
| cttgagagta accagtaaaa gtaaggagtc ggggctgtct gatgtcagca | | |
| ggcccagttt ctgccattcc agctgtgggc acgtcagcga aggcaagcgc | | |
| aggttcacct acgaccacgc tgagctggaa aggaaaatcg cgtgctgctc | | |
| cccgccccca gactacaact cggtggtcct gtactccacc ccacccatct agagtttgac | | |
| acgaagcctt atttctagaa gcacatgtgt atttataccc ccaggaaact agcttttgcc | | |
| agtattatgc atatataagt ttacaccttt atctttccat gggagccagc tgctttttgt | | |
| gatttttttta atagtgcttt tttttttttg actaacaaga atgtaactcc agatagagaa | | |
| atagtgacaa gtgaagaaca ctactgctaa atcctcatgt tactcagtgt tagagaaatc | | |
| cttcctaaac ccaatgactt ccctgctcca acccccgcca cctcagggca | | |
| cgcaggacca gtttgattga ggagctgcac tgatcaccca atgcatcacg | | |
| taccccactg ggccagccct gcagcccaaa acccagggca acaagcccgt | | |
| tagccccagg gatcactggc tggcctgagc aacatctcgg gagtcctcta | | |
| gcaggcctaa gacatgtgag gaggaaaagg aaaaaaagca aaaagcaagg | | |
| gagaaaagag aaaccgggag aaggcatgag aaagaatttg agacgcacca | | |
| tgtgggcacg gagggggacg gggctcagca atgccatttc agtggcttcc | | |
| cagctctgac ccttctacat ttgagggccc agccaggagc agatggacag | | |
| cgatgagggg acattttctg gattctggga ggcaagaaaa ggacaaatat ctttttttgga | | |
| actaaagcaa attttagaac tttacctatg gaagtggttc tatgtccatt ctcattcgtg | | |
| gcatgttttg atttgtagca ctgagggtgg cactcaactc tgagcccata cttttggctc | | |
| ctctagtaag atgcactgaa aacttagcca gagttaggtt gtctccaggc catgatggcc | | |
| ttacactgaa aatgtcacat tctattttgg gtattaatat atagtccaga cacttaactc | | |
| aatttcttgg tattattctg ttttgcacag ttagttgtga aagaaagctg agaagaatga | | |
| aaatgcagtc ctgaggagag gagttttctc catatcaaaa cgagggctga | | |
| tggaggaaaa aggtcaataa ggtcaaggga aaaccccgtc tctataccaa | | |
| ccaaaccaat tcaccaacac agttgggacc caaaacacag gaagtcagtc | | |
| acgtttcctt ttcatttaat ggggattcca ctatctcaca ctaatctgaa aggatgtgga | | |
| agagcattag ctggcgcata ttaagcactt taagctcctt gagtaaaaag gtggtatgta | | |
| atttatgcaa ggtatttctc cagttgggac tcaggatatt agttaatgag ccatcactag | | |
| aagaaaagcc cattttcaac tgctttgaaa cttgcctggg gtctgagcat gatgggaata | | |
| gggagacagg gtaggaaagg gcgcctactc ttcagggtct aaagatcaag | | |
| tgggccttgg atcgctaagc tggctctgtt tgatgctatt tatgcaagtt agggtctatg | | |
| tatttatgat gtctgcacct tctgcagcca gtcagaagct ggagaggcaa cagtggattg | | |
| ctgcttcttg gggagaagag tatgcttcct tttatccatg taatttaact gtagaacctg | | |
| agctctaagt aaccgaagaa tgtatgcctc tgttcttatg tgccacatcc ttgtttaaag | | |
| gctctctgta tgaagagatg ggaccgtcat cagcacattc cctagtgagc ctactggctc | | |
| ctggcagcgg cttttgtgga agactcacta gccagaagag aggagtggga | | |
| cagtcctctc caccaagatc taaatccaaa caaaagcagg ctagagccag | | |
| aagagaggac aaatctttgt tcttcctctt ctttacatac gcaaaccacc tgtgacagct | | |
| ggcaatttta taaatcaggt aactggaagg aggttaaaca cagaaaaaag | | |
| aagacctcag tcaattctct actttttttt tttttccaa atcagataat agcccagcaa | | |
| atagtgataa caaataaaac cttagctatt catgtcttga tttcaataat taattcttaa | | |
| tcattaagag accataataa atactccttt tcaagagaaa agcaaaacca ttagaattgt | | |
| tactcagctc cttcaaactc aggtttgtag catacatgag tccatccatc agtcaaagaa | | |
| tggttccatc tggagtctta atgtagaaag aaaaatggag acttgtaata atgagctagt | | |
| tacaaagtgc ttgttcatta aaatagcact gaaaattgaa acatgaatta actgataata | | |
| ttccaatcat ttgccattta tgacaaaaat ggttggcact aacaaagaac gagcacttcc | | |
| tttcagagtt tctgagataa tgtacgtgga acagtctggg tggaatgggg ctgaaaccat | | |
| gtgcaagtct gtgtcttgtc agtccaagaa gtgacaccga gatgttaatt ttagggaccc | | |
| gtgccttgtt tcctagccca caagaatgca aacatcaaac agatactcgc tagcctcatt | | |
| taaattgatt aaaggaggag tgcatctttg gccgacagtg gtgtaactgt atgtgtgtgt | | |
| gtgtgtgtgt gtgtgtgtgt gtgtgtgggt gtatgtgtgt tttgtgcata actatttaag | | |
| gaaactggaa ttttaaagtt acttttatac aaaccaagaa tatatgctac agatataaga | | |
| cagacatggt ttggtcctat atttctagtc atgatgaatg tattttgtat accatcttca | | |
| tataataaac ttccaaaaac aca | | |

TABLE III-continued

| Sequence | Name | SEQ ID |
|---|---|---|
| mvsywdtgvl lcallsclll tgsssgsklk dpelslkgtq himqagqtlh lqcrgeaahk<br>wslpemvske serlsitksa cgrngkqfcs tltintaqan htgfysckyl avptskkket<br>esaiyifisd tgrpfvemys eipeiihmte grelvipcrv tspnitvtlk kfpldtlipd<br>gkriiwdsrk gfiisnatyk eiglltceat vnghlyktny lthrqtntii dvqistprpv<br>kllrghtlvl nctattplnt rvqmtwsypd eknkrasvrr ridqsnshan ifysvltidk<br>mqnkdkglyt crvrsgpsfk svntsvhiyd kafitvkhrk qqvletvagk rsyrlsmkvk<br>afpspevvwl kdglpateks aryltrgysl iikdvteeda gnytillsik qsnvfknlta<br>tlivnvkpqi yekavssfpd palyplgsrq iltctaygip qptikwfwhp cnhnhsearc<br>dfcsnneesf ildadsnmgn riesitqrma ilegknkmas tlvvadsris giyiciasnk<br>vgtvgrnisf yitdvpngfh vnlekmpteg edlklsctvn kflyrdvtwi llrtvnnrtm<br>hysiskqkma itkehsitln ltimnvslqd sgtyacrarn vytgeeilqk keitirdqea<br>pyllrnlsdh tvaissttl dchangvpep qitwfknnhk iqqepgiilg pgsstlfier<br>vteedegvyh ckatnqkgsv essayltvqg tsdksnleli tltctcvaat lfwilltlfi<br>rkmkrsssei ktdylsiimd pdevpldeqc erlpydaskw efarerlklg kslgrgafgk<br>vvqasafgik ksptortvav kmlkegatas eykalmtelk ilthighhin vvnllgactk<br>qggplmvive yckygnlsny lkskrdlffl nkdaalhmep kkekmepgle<br>qgkkprldsv tssesfassg fqedkslsdv eeeedsdgfy kepitmedli<br>sysfqvargm eflssrkcih rdlaarnill sennvvkicd fglardiykn pdyvrkgdtr<br>lplkwmapes ifdkiystks dvwsygvllw eifslggspy pgvqmdedfc<br>srlregmrmr apeystpeiy qimldcwhrd pkerprfael veklgdliqa nvqqdgkdyi<br>pinailtgns gftystpafs edffkesisa pkfnsgssdd vryvnafkfm slerikffee<br>llpnatsmfd dyqgdsstll aspmlkrftw tdskpkaslk idlrvtsksk esglsdvsrp<br>sfchsscghv segkrrftyd haelerkiac cspppdynsv vlystppi | Full-length human VEGFR1 protein | SEQ ID NO: 2 |
| atggtcagct actgggacac cggggtcctg ctgtgcgcgc tgctcagctg tctgcttctc<br>acaggatcta gttcaggttc aaaattaaaa gatcctgaac tgagtttaaa<br>aggcacccag cacatcatgc aagcaggcca gacactgcat ctccaatgca<br>gggggaagc agcccataaa tggtctttgc ctgaaatggt gagtaaggaa<br>agcgaaaggc tgagcataac taaatctgcc tgtggaagaa atggcaaaca<br>attctgcagt actttaacct tgaacacagc tcaagcaaac cacactggct tctacagctg<br>caaatatcta gctgtaccta cttcaaagaa gaaggaaaca gaatctgcaa tctatatatt<br>tattagtgat acaggtagac ctttcgtaga gatgtacagt gaaatccccg aaattataca<br>catgactgaa ggaagggagc tcgtcattcc ctgccgggtt acgtcaccta acatcactgt<br>tactttaaaa aagtttccac ttgacacttt gatccctgat ggaaaacgca taatctggga<br>cagtagaaag ggcttcatca tatcaaatgc aacgtacaaa gaaatagggc<br>ttctgacctg tgaagcaaca gtcaatgggc atttgtataa gacaaactat ctcacacatc<br>gacaaaccaa tacaatcata gatgtccaaa taagcacacc acgcccagtc<br>aaattactta gaggccatac tcttgtcctc aattgtactg ctaccactcc cttgaacacg<br>agagttcaaa tgacctggag ttaccctgat gaaaaaaata agagagcttc<br>cgtaaggcga cgaattgacc aaagcaattc ccatgccaac atattctaca gtgttcttac<br>tattgacaaa atgcagaaca aagacaaagg actttatact tgtcgtgtaa<br>ggagtggacc atcattcaaa tctgttaaca cctcagtgca tatatatgat aaagcattca<br>tcactgtgaa acatcgaaaa cagcaggtgc ttgaaaccgt agctggcaag<br>cggtcttacc ggctctctat gaaagtgaag gcatttccct cgccggaagt tgtatggtta<br>aaagatgggt tacctgcgac tgagaaatct gctcgctatt tgactcgtgg ctactcgtta<br>attatcaagg acgtaactga agaggatgca gggaattata caatcttgct<br>gagcataaaa cagtcaaatg tgtttaaaaa cctcactgcc actctaattg tcaatgtgaa<br>accccagatt tacgaaaagg ccgtgtcatc gtttccagac ccggctctct acccactggg<br>cagcagacaa atcctgactt gtaccgcata tggtatccct caacctacaa tcaagtggtt<br>ctggcacccc tgtaaccata atcattccga agcaaggtgt gacttttgtt ccaataatga<br>agagtccttt atcctggatg ctgacagcaa catgggaaac agaattgaga<br>gcatcactca gcgcatggca ataatagaag gaaagaataa gcttccacca<br>gctaacagtt ctttcatgtt gccacctaca agcttctctt ccaactactt ccatttcctt<br>ccgtga | Soluble human VEGFR1 mRNA | SEQ ID NO: 3 |
| mvsywdtgvl lcallscill tgsssgsklk dpelslkgtq himqagqtlh lqcrgeaahk<br>wslpemvske serlsitksa cgrngkqfcs tltintaqan htgfysckyl avptskkket<br>esaiyifisd tgrpfvemys eipeiihmte grelvipcrv tspnitvtlk kfpldtlipd<br>gkriiwdsrk gfiisnatyk eiglltceat vnghlyktny lthrqtntii dvqistprpv<br>kllrghtlvl nctattplnt rvqmtwsypd eknkrasvrr ridqsnshan ifysvltidk<br>mqnkdkglyt crvrsgpsfk svntsvhiyd kafitvkhrk qqvletvagk rsyrlsmkvk<br>afpspevvwl kdglpateks aryltrgysl iikdvteeda gnytillsik qsnvfknlta<br>tlivnvkpqi yekavssfpd palyplgsrq iltctaygip qptikwfwhp cnhnhsearc<br>dfcsnneesf ildadsnmgn riesitqrma ilegknklpp anssfmlppt sfssnyfhflp | Soluble human VEGFR1 protein | SEQ ID NO: 4 |

EXAMPLE

Dose-Dependent Inhibition of VEGF-A/VEGFR1 and PIGF/VEGFR-1 Interaction.

The assay to test the binding of PIGF or VEGF-A with the VEGFR-1 receptor is based on the ELISA method [Ponticelli et al., JBC. 2008 Dec. 5; 283 (49): 34250-9] and was performed using reagents acquired from R&D Systems.

The human recombinant receptor VEGFR-1, in particular the form consisting of the seven extracellular domains of the receptor fused to the Fc domain of human IgG (R&D Systems, cat N° 321-FL), was made to adhere in the wells of 96-well microplates at a concentration of 0.5 g/ml in PBS pH 7.5 (100 μl/well) for 16 hours at room temperature (RT).

After the non-specific binding sites had been blocked in the wells using a buffer solution consisting of PBS pH 7.5 containing 3% BSA, 5 ng/ml of recombinant PIGF (R&D Systems, cat N° 264-PG), or 5 ng/ml of recombinant VEGF-A (R&D Systems, cat N° 293-VE) of human origin in PBET (PBS pH 7.5, BSA 0.1%, EDTA 5 mM, polysorbate 80 0.004% (TWEEN 80)) were added to the wells with the adhered receptor.

Simultaneously with the ligands, i.e., PIGF or VEGF-A, graduated doses of iVR1, iVR1-Cys or a control peptide (PC-[(S-Ser)-(S-Ala)-(S-Cha) tripeptide with a tetrameric structure identical to the structure of the iVR1 peptides]) were added at concentrations comprised between 780 and 50000 nM. The binding reaction was conducted for one hour at 37° C., followed by one hour at room temperature.

At the end of the binding and/or competition step, anti-human-PIGF biotinylated polyclonal antibodies (R&D Systems, cat No. BAF264) or anti-human-VEGF-A (R&D Systems, cat No. BAF293) were added to the wells at the concentration of 300 ng/ml in PBET. After one hour of incubation at 37° C. followed by one hour at room temperature, an HRP-conjugated avidin-streptavidin system (Vectastain elite ABC kit) and a substrate for HRP (o-phenylenediamine-Sigma, cat No. P1526) were added to the wells. Quantization was performed by determining the absorbance at 490 nM.

Any inhibitory activity of the peptides was expressed in terms of % of residual binding, comparing the data obtained for the binding of PIGF or VEGF-A to the receptors in the presence of the tetrameric peptides with those in the absence of the same. iVR1 represented the positive control of the inhibition of the PIGF/VEGFR-1 or VEGF-A/VEGFR-1 interaction.

The results are given in Tables IV and V and show that iVR1-Cys demonstrated a capacity to inhibit the interaction both of PIGF and VEGF-A with VEGFR-1 in a dose-dependent manner.

The concentration at which iVR1-Cys is capable of inhibiting the interaction of PIGF with VEGFR-1 by 50% ($IC_{50}$) is below 1000 nM, whereas the IC50 for VEGF-A/VEGFR-1 is close to or just above 1000 nM.

Therefore, iVR1-Cys has an inhibitory capacity that is about 10 times greater than that of iVR1, and it is thus expected that it can be used at doses that are 10 times smaller in the same in vitro and in vivo experimental protocols relating to angiogenesis/neoangiogenesis inhibition in order to obtain the same effects as obtained with IVR1.

PC gives no inhibition.

TABLE IV

Dose-dependent inhibition of PIGF/VEGFR-1 interaction

| peptides | binding % | | |
|---|---|---|---|
| [nM] | iVR1-Cys | iVR1 | PC |
| 780 | 83.82 | 99.36 | 98.88 |
| 1560 | 35.50 | 101.32 | 102.35 |
| 3125 | 25.54 | 96.10 | 99.53 |
| 6250 | 14.09 | 68.49 | 93.82 |
| 12500 | 12.59 | 44.57 | 87.21 |
| 25000 | 10.27 | 36.02 | 88.55 |
| 50000 | 9.18 | 26.26 | 90.16 |

TABLE V

Dose-dependent inhibition of VEGF-A/VEGFR-1 interaction

| peptides | binding % | | |
|---|---|---|---|
| [nM] | iVR1-Cys | iVR1 | PC |
| 780 | 92.32 | 98.36 | 100.09 |
| 1560 | 43.71 | 96.21 | 102.59 |
| 3125 | 21.70 | 93.93 | 95.20 |
| 6250 | 12.50 | 66.00 | 91.37 |
| 12500 | 9.81 | 37.02 | 100.04 |
| 25000 | 7.99 | 21.45 | 93.44 |
| 50000 | 6.50 | 8.60 | 87.93 |

The capacity of tetrameric peptides having formula (II), but with Y2 different from D-cysteine, to inhibit VEGF-A/VEGFR-1 binding was assessed with the binding assay described above. Y2 of the peptides and the respective $IC_{50}$ of inhibition of VEGF-A/VEGFR-1 interaction are indicated in Table VI.

TABLE VI $IC_{50}$ of inhibition of the interaction VEGF-A/VEGFR-1

| Y2 | $IC_{50}$, μM |
|---|---|
| L-cysteine | 2.03 ± 0.2 |
| L-methionine | 2.15 ± 1.0 |
| D-methionine | 2.89 ± 1.2 |
| L-methionine sulfoxide | 15.7 ± 2.1 |
| L-methionine sulfone | 4.62 ± 1.4 |
| D-serine | 2.43 ± 03 |
| L-serine | 2.90 ± 0.5 |
| D-threonine | 2.60 ± 0.6 |
| L-threonine | 1.29 ± 0.5 |

Inhibition of PIGF-Induced Phosphorylation of VEGFR-1.

An assay of the PIGF-induced phosphorylation of the receptor VEGFR-1 was performed in order to evaluate the inhibitory capacity of the peptide iVR1-Cys and compare its activity to that of iVR1.

For the activation of VEGFR-1, use was made of a cell line over-expressing the receptor, called 293-VEGFR-1, obtained by stable transfection from HEK-293 cells (Errico, M. et al. 2004 JBC, 279:43929-43939).

For this purpose, the 293-VEGFR-1 cells were cultured until reaching subconfluence and the cells were subsequently ‘starved’, by keeping/incubating them in the culture medium without serum for at least 16 hours.

At the end of the starvation step, the culture medium was removed and the cell monolayers were incubated with $Na_3VO_4$ 100 μM for 5 minutes in order to inhibit the activity of the endogenous phosphatase.

The cells were then stimulated with PIGF (1) alone at 20 ng/ml in the medium used for the starvation for 10 minutes at 37° C. and (2) in the presence of the peptides at the concentration of 5 μM.

An anti-human-PIGF neutralizing monoclonal antibody (Thrombogenics) was used at a concentration of 3.3 nM as an inhibition control. PBS was used as a negative control.

At the end of incubation, the cells were washed with cold $Na_3VO_4$ 100 μM and then lysed in the buffer composed of Tris-HCl 20 mM pH 8, EDTA 5 mM, NaCl 150 mM, 1% Triton-X100, 10% glycerol, zinc acetate 10 mM, $Na_3VO_4$ 100 μM and a mixture of protease inhibitors and incubated for 1 hour at 4° C. under gentle stirring. At the end, the cell lysates were centrifuged at 12000×g for 15 minutes to remove the cellular debris. Quantization of the extracts was performed with the Bradford method using a Bio-Rad reagent. 100 μg of every protein extract were loaded on SDS-PAGE reducing to 8.5%, and then the standard method for analyzing proteins was carried out by western blotting.

The anti-p-VEGFR-1 antibody (R&D Systems, cat. N° AF4170), diluted 1:500, was used to detect the phosphorylated VEGFR-1, whilst normalization was carried out by detecting the non-phosphorylated form of the receptor using the anti-VEGFR-1 antibody (Sigma-Aldrich, cat. No. V4262) diluted 1:500.

Figure 1:
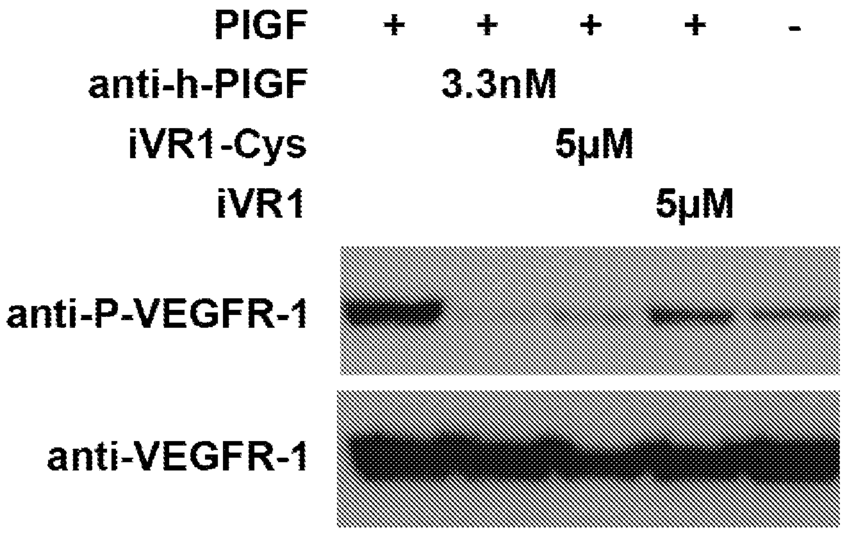
FIG. 1 shows the inhibitory activity of iVR1 and iVR1-Cys and of the anti-PIGF monoclonal antibody with reference to PIGF-induced phosphorylation of VEGFR-1. The analysis of VEGFR-1 phosphorylation induced with 20 ng/ml of PIGF was conducted on 293-VEGFR-1 cells by western blotting. iVR1-Cys and iVR1 were added simultaneously to PIGF at a concentration of 5 μM. A human anti-PIGF neutralizing monoclonal antibody was used at a concentration of 3.3 nM as an inhibition control. PBS was used as a negative control.

As shown in FIG. 1, the peptide iVR1-Cys, used at a concentration about 5 times higher (5000 nM) than its $IC_{50}$ determined in the binding assays (see Example 1), brings about a powerful inhibition of phosphorylation of the receptor, similar to the one obtained with the neutralizing antibody and decidedly greater than the one obtained with iVR1 using the same concentration.

Inhibition of Choroidal Neovascularization by Intravitreal and Oral (Gavage) Administration of iVR1 and iVR1-Cys.

The experimental model of laser-induced choroidal neovascularization entails generating damage to Bruch's membrane, which separates the choroid from the pigmented epithelium of the retina (RPE). The damage is provoked by laser-induced burning, which causes the perforation of Bruch's membrane, thus activating chorioretinal vascularization, the growth of new vessels which, starting from the choroid, invade the overlying retinal tissue. This mouse model sums up the main characteristics of the exudative form of human age-related macular degeneration (AMD) and is in fact commonly used as a preclinical model of AMD. It enables an assessment of the anti-angiogenic activity of the molecules of interest.

In order to be able to visualize the ocular fundus of the mouse and induce damage with the laser, the Micron IV integrated system was used, following the experimental procedure described below.

First of all, dilatation of the animal's pupil was induced by applying 0.5% Tropicamide eye drops. The animal was then anaesthetized by intraperitoneal injection of a solution of ketamine and xylazine (80 mg/Kg and 10 mg/Kg, respectively). Once sedated, the animal was placed on the stand and a hydroxypropyl methylcellulose 2.5% aqueous solution was applied on both eyes. It has the dual function of preventing dehydration of the cornea and improving visualization of the ocular fundus by placing the camera lens of the Micron IV in contact with the solution (a procedure similar to the one used in microscopy with immersion objectives).

In order to induce damage with the laser, first of all the laser pointer is activated and focused so as to apply the laser beam using the RPE layer as a reference. The area where the laser beam is applied must be distant from the main vessels of the retina in order to prevent possible hemorrhaging. The efficiency of the burning at the level of Bruch's membrane is confirmed by the formation of a bubble immediately after application of the laser beam. The conditions of application of the laser beam were 200 mW of power for 100 msec.

From data present in the literature, well summarized in the article by Lambert et al. (Nature Protocols, 2013, 8:2197), it is known that the maximum neo-vascularization in this experimental model is obtained seven days after the damage.

C57BI6/J mice were used, n=5 per group. At the end of the procedure of inducing damage with the laser, an intravitreal injection was immediately performed and 10 and 50 μg of iVR1-Cys or iVR1, and 50 μg of PC in 1 μL of DMSO were administered using a Hamilton syringe with a 32 g needle. As a control DMSO was injected on its own.

After seven days the animals were sacrificed and the eyes were enucleated and fixed in 4% paraformaldehyde. Subsequently, the front segment of the eye, consisting of the: cornea, iris and crystalline was removed under a stereo microscope. The remaining part, defined 'eye-cups' or posterior segment consisting of: sclera, choroid, RPE and retina was incubated in the presence of 0.7% FITC-Griffonia simplicifolia Isolectin B4 (Vector Laboratories, Burlingame, CA) for sixteen hours. After a series of washes, the retina is removed and four cuts are made on the RPE/choroid, which enables mounting on the slide for observation under a fluorescence microscope. Quantization of choroidal neovascularization is performed in terms of volume. In order to assess the volume of every spot, a series of images is acquired (Z-Satcks, about 20-25 image), each with a thickness of 1 μm, from the upper surface to the deepest focal plane, at the level of the RPE cells. The volume of fluorescence is measured by means of the ImageJ program (NIH, Bethesda, MD), taking the sum of the areas of fluorescence of every single plane.

Figure 2:
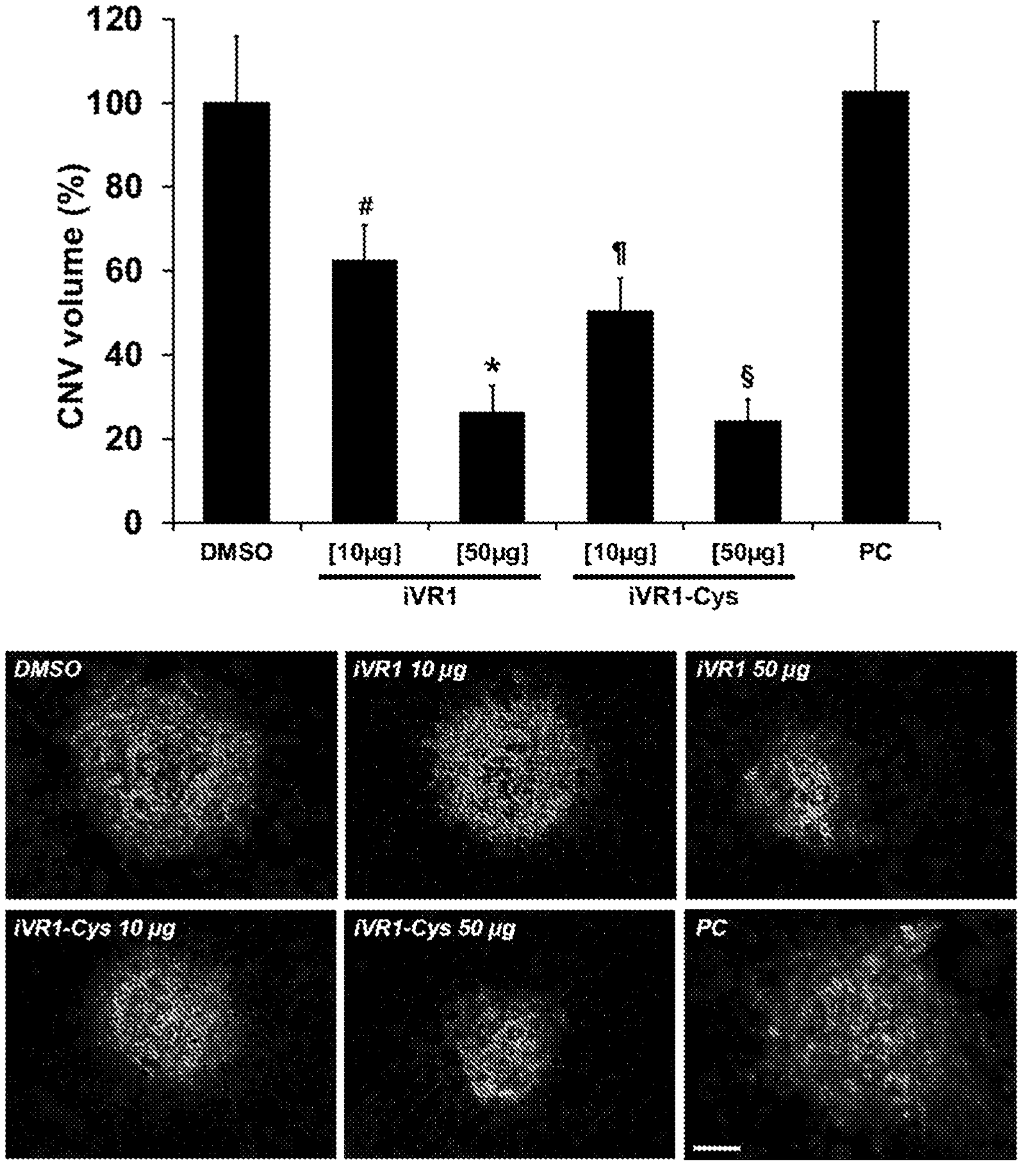
FIG. 2 shows that intravitreally administered iVRI-Cys inhibits laser-induced choroidal neovascularization in a dose-dependent manner. A single intravitreal injection of 10 or 50 μg of iVRI-Cys brings about a dose-dependent reduction of choroidal neovascularization equal to 48.9% and 75.9% compared to injection of the vehicle (DMSO). The same amounts of iVR1 bring about an inhibition of CNV equal to 37.8% and 73.9%. The control peptide (PC) shows no inhibitory capacity. Quantization of the volume of neovascularization was performed on n=12 and 15 spots for iVR1 10 μg and 50 μg; on n=10 and 8 spots for iVR1-Cys 10 μg and 50 μg; n=15 spots for PC and n=14 spots for the DMSO. The data are represented as the mean±SEM relative to the control. #p<0.05; *p>0.0002; ¶p<0.02; § p>0.002; vs PC and DMSO. At the bottom, images representative of CNV. The bar represents 100 μm.

Quantization of CNV was performed on n=12 and 15 spots for iVR1 10 μg and 50 μg; n=10 and 8 spots for iVR1-Cys 10 μg and 50 μg; n=15 spots for PC and n=14 spots for DMSO. The results given in FIG. 2 show that both peptides are capable of bringing about a dose-dependent inhibition of neovascularization. With the higher dose (50 μg), a powerful, significant and comparable neovascularization inhibition capacity was obtained: iVR1-Cys −75.9% and −74.6% vs the vehicle and PC ($p>0.002$); iVR1 −73.9% and −76.5% vs the vehicle and PC ($p>0.0002$).

At the dosage of 10 μg, iVR1 brings about a 37.8% and 39.3% inhibition of neovascularization vs the vehicle and PC ($p<0.05$), whereas iVR1-Cys brings about a 48.9% and 51.0% inhibition vs the vehicle and PC ($p<0.02$). At a low concentration, therefore, the peptide iVR1-Cys demonstrates a greater inhibition effectiveness than the peptide iVR1, as it brings about a further 19.3% reduction of neovascularization. It is thus possible that the maximum threshold of the inhibitory capacity of the peptides was reached at the higher dosage used.

For the experiments on oral administration (gavage), choroidal neovascularization was induced in C57BI6/J mice, n=5 animals per group, following the experimental procedure previously described. The administration of the peptides iVR1 and iVR1-Cys and of the vehicle began immediately after induction of the damage, as soon as the animals recovered from the anesthesia, twice a day for the seven days provided for by the experimental protocol. The peptides were administered at 50 mg/Kg, on the basis of the data obtained previously for the peptide iVR1 administered intraperitoneally (Cicatiello et al. 2015, Oncotarget, 6, 10563-10576).

To enable oral administration to be performed, the peptides were dissolved in DMSO, and then mixed with Nutilis food thickener, so as to have a final mixture consisting of 9 parts Nutilis and 1 part DMSO.

The substances were prepared at a concentration such as to make it possible to use, for every single administration, 200 μl of the 9:1 Nutilis/substance in DMSO mixture, which was administered directly into the animal's stomach using a suitable needle for gavage with a 20 gauge opening. In the control group, 200 μl of the 9:1 Nutilis/DMSO mixture were administered.

At the end of the experiment, the animals were sacrificed, the eyes were removed and dissected to isolate the RPE-choroid and to determine the volume of CNV by immunofluorescence analysis, as described below.

Quantization of CNV was performed on n=18 spots for iVR1-Cys, n=20 spots for iVR1 and n=10 spots for the vehicle.

The results are given in FIG. 3 and demonstrate that the peptide iVR1-Cys is capable of inducing a significant inhibition of neovascularization compared to the vehicle (−45.9%, p=0.007), at levels similar to those observed for iVR1 (−49.7%, p=0.001).

Serum Protease Stability of iVR1-Cys.

The stability of the peptide iVR1-Cys in 10% serum (fetal calf serum, FCS) in a 50 mM phosphate buffer solution, pH 7.3, at 168 h was determined as described by Ponticelli et al., relying on a method based on RP-HPLC chromatography, described therein [Ponticelli et al., J Biol Chem. 2008 Dec. 5; 283 (49): 34250-9].

The reference curve was constructed by dissolving the compound in DMSO at increasing concentrations of between 0.1 μmol/L and 1000 μmol/L in order to have complete dissolution. The concentration of the molecule left in contact with 10% FCS at the initial concentration of 10 μmol/L was then determined by drawing 3 aliquots at time t=0, then every hour in the first 12 hours and then at 24, 72, 120, and 168 h. The aliquots were diluted 1:1 with acetic acid 0.1 M in order to detach any peptide bound to the albumin, centrifuged to remove any precipitated materials and analyzed by RP-HPLC under the conditions reported in Ponticelli et al. The amount of residual peptide detected in the aliquots, expressed as a percentage relative to the initial amount, was plotted as a function of time. The results are shown in Table VII as the mean of the three determinations±the standard deviation (SD).

TABLE VII

| Time (h) | % residual peptide ± SD |
|---|---|
| 0 | 101 ± 4 |
| 1 | 100 ± 11 |
| 2 | 99 ± 7 |
| 3 | 98 ± 5 |
| 4 | 97 ± 4 |
| 5 | 96 ± 5 |
| 6 | 99 ± 6 |
| 7 | 95 ± 8 |
| 8 | 96 ± 5 |
| 9 | 95 ± 6 |
| 10 | 94 ± 10 |
| 11 | 94 ± 8 |
| 12 | 93 ± 4 |
| 24 | 93 ± 6 |
| 72 | 92 ± 7 |
| 120 | 91 ± 5 |
| 168 | 92 ± 8 |

The invention claimed is:

1. A method of treating a neovascular eye disease selected from the group consisting of macular edema, the wet form of age-related macular degeneration, retinopathy of prematurity, central retinal vein occlusions, vitreous hemorrhage, retinal detachment and combinations thereof, comprising administering a peptide orally or by gavage to a mammal in need thereof, wherein said peptide is isolated and consists of formula (IIa)

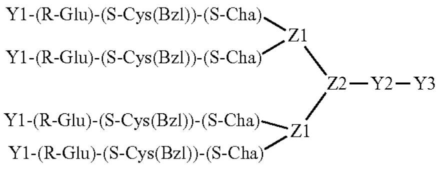

wherein

Y1 is an amino-terminal peptide functional group ($NH_2$);

Glu is glutamic acid;

Cys(Bzl) is benzyl cysteine;

Cha is cyclohexylalanine;

Y2 is glycine;

Y3 is selected from the group consisting of a carboxylic group, a carboxyamide group, an N-methyl-substituted carboxyamide, a di-substituted N, N-dimethyl group, a hydroxyl group, and hydrogen;

Z1 and Z2 indicate a trifunctional molecule having the following formula

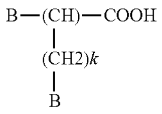

wherein k is 4 and B is an amino group.

2. The method according to claim 1 wherein Z1 and Z2 are each selected from S-lysine and R-lysine.

3. The method according to claim 1 wherein the peptide is formula (IIc):

(Formula IIc)

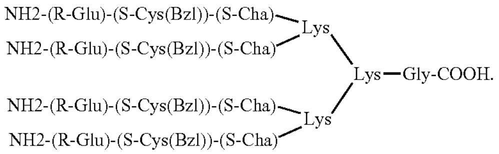

4. The method according to claim 1, wherein an effective amount of the peptide is between 10 and 2000 mg/dose.

5. The method according to claim 1, wherein said oral or gavage administration provides for a single dose or multiple doses.

* * * * *